US010786690B2

(12) United States Patent
Boeglin et al.

(10) Patent No.: US 10,786,690 B2
(45) Date of Patent: Sep. 29, 2020

(54) AMIDE DERIVATIVES OF POLYCAFFEOYLQUINIC ACIDS, PROCESS FOR PRODUCING SAME AND USES THEREOF

(71) Applicant: TEMISIS, Vandoeuvre-les-Nancy (FR)

(72) Inventors: Damien Boeglin, Ostwald (FR); Pierre Warnault, Blainville sur l'Eau (FR)

(73) Assignee: TEMISIS, Vandoeuvre-les-Nancy (FR)

( * ) Notice: Subject to any disclaimer, the term of this patent is extended or adjusted under 35 U.S.C. 154(b) by 0 days.

(21) Appl. No.: 16/096,519

(22) PCT Filed: Apr. 26, 2017

(86) PCT No.: PCT/EP2017/059898
§ 371 (c)(1),
(2) Date: Oct. 25, 2018

(87) PCT Pub. No.: WO2017/186779
PCT Pub. Date: Nov. 2, 2017

(65) Prior Publication Data
US 2019/0134432 A1    May 9, 2019

(30) Foreign Application Priority Data
Apr. 26, 2016   (FR) .................................... 16 53693

(51) Int. Cl.
| A61Q 19/08 | (2006.01) |
| C07C 231/02 | (2006.01) |
| C07C 235/40 | (2006.01) |

(52) U.S. Cl.
CPC ............ A61Q 19/08 (2013.01); C07C 231/02 (2013.01); C07C 235/40 (2013.01); C07B 2200/07 (2013.01); C07C 2601/14 (2017.05)

(58) Field of Classification Search
None
See application file for complete search history.

(56) References Cited

U.S. PATENT DOCUMENTS 2,918,477 A    12/1959   Alberti et al.
2004/0170581 A1    9/2004   Henry et al.
(Continued)

FOREIGN PATENT DOCUMENTS

CN    105130838 A    12/2015
EP    1 260 212 A1    11/2002
(Continued)

OTHER PUBLICATIONS

Tian ("Structural modification and biological evaluation of monomeric compound from Padanus tectorius" Zhongcaoyao/Chinese Traditional and Herbal Drugs, vol. 46, 2015, p. 1133-1139) (Year: 2015).*

(Continued)

Primary Examiner — Amy C Bonaparte
(74) Attorney, Agent, or Firm — Birch, Stewart, Kolasch & Birch, LLP

(57) ABSTRACT

The present invention thus relates to amide derivatives of polysubstituted quinic acids (abbreviated to "QPS"), of general formula (IA): (IA), in which $—R_{1A}$ and $R_{2A}$ are, independently of one another: H, with the proviso that $R_{1A}$ and $R_{2A}$ are not both a hydrogen atom, a butyl group, a $C_7-C_{30}$ alkyl group, $—a$ $C_7-C_{30}$ alkylaryl or arylalkyl group, or a $C_7-C_{18}$ aryl group; and $—Q_1$, $Q_3$, $Q_4$ and $Q_5$ are, independently of one another, an OH, caffeoyl, maloyl, caffeoylmaloyl ou maloylcaffeoyl group, with the proviso that at least one of these radicals is not an OH group, or to a pharmaceutically acceptable salt or stereoisomer or hydrate thereof, and also to the process for producing same, to the use thereof as a medicament, in particular for the treatment and/or prevention of inflammation and of inflammatory diseases, and to the pharmaceutical, cosmetic and nutraceutical compositions containing same.

25 Claims, 7 Drawing Sheets

(56) References Cited

U.S. PATENT DOCUMENTS

2010/0144828 A1* 6/2010 Wu .................. C07C 231/02
514/423
2014/0371445 A1 12/2014 Chen et al.

FOREIGN PATENT DOCUMENTS

| EP | 2128125 A1 | 12/2009 |
| FR | 3047171 A1 | 8/2017 |
| WO | WO 2010/132504 A1 | 11/2010 |
| WO | WO 2015/013422 A1 | 1/2015 |

OTHER PUBLICATIONS

Definition of "naphthenic hydrocarbon", downloaded from https://www.glossary.oilfield.slb.com/en/Terms/n/naphthenic_hydrocarbon.aspx on Mar. 31, 2020 (Year: 2020).*
Barañano et al., "Biliverdin reductase: A major physiologic cytoprotectant", PNAS, vol. 99, No. 25, Dec. 10, 2012, pp. 16093-16098 (6 pages).
Fitzpatrick et al., "Caffeic Acid Phenethyl Ester, an Inhibitor of Nuclear Factor-kB, Attenuates Bacterial Peptidoglycan Polysaccharide-Induced Colitis in Rats", the Journal of Pharmacology and Experimental Therapeutics, vol. 299, No. 3, 2001, pp. 915-920 (6 pages).
Guenin-Macé et al., "Shaping mycolactone for therapeutic use against inflammatory disorders", Sci. Transl. Med., vol. 7, Issue 289, May 2015 (published May 27, 2015), 8 pages.
Jerabek et al., "OCT4: Dynamic DNA binding pioneers stem cell pluripotency", Biochimica et Biophysica Acta, vol. 1839, 2014, pp. 138-154 (17 pages).
Krieg et al., "The extracellular matrix of the dermis: flexible structures with dynamic functions", Experimental Dermatology, vol. 20, 2011, pp. 689-695 (7 pages).
Kroeze et al., "Chemokine-Mediated Migration of Skin-Derived Stem Cells: Predominant Role for CCL5/RANTES", The Society for Investigative Dermatology, vol. 129, 2009 (published online Jan. 1, 2009), pp. 1569-1581 (13 pages).
Lee et al., "3,4,5-Tricaffeoylquinic Acid Inhibits the Lipopolysaccharide-Stimulated Production of Inflammatory Mediators in Keratinocytes", Pharmacology, vol. 90, 2012 (published online Aug. 29, 2012), pp. 183-192 (10 pages).
Otterbein et al., "MKK3 Mitogen-Activated Protein Kinase Pathway Mediates Carbon Monoxide-Induced Protection Against Oxidant-Induced Lung Injury", American Journal of Pathology, vol. 163, No. 6, Dec. 2003, pp. 2555-2563 (9 pages).
Peluso et al., "Studies on the Inhibitory Effects of Caffeoylquinic Acids on Monocyte Migration and Superoxide Ion Production", Journal of Natural Products, vol. 58, No. 5, May 1995, pp. 639-646 (1 page), abstract only provided.
Stevens et al., "A secreted MMP is required for reepithelialization during wound healing", Molecular Biology of the Cell, vol. 23, Mar. 15, 2012 (published online Jan. 19, 2012), pp. 1068-1079 (12 pages).
Stocker et al., "Antioxidant activity of albumin-bound bilirubin", Proc. Natl. Acad. Sci., vol. 84, USA, Aug. 1987, pp. 5918-5922 (5 pages).
Wang et al., "Cytoprotective effect of caffeic acid phenehtyl ester (CAPE) and catechol ring-fluorinated CAPE derivatives against menadione-induced oxidative stress in human endothelial cells", Bioorganic & Medicinal Chemistry, vol. 14, 2006 (published online Mar. 31, 2006), pp. 4879-4887 (9 pages).
Wang et al., "Structure-activity relationships in the cytoprotective effect of caffeic acid phenethyl ester (CAPE) and fluorinated derivatives: Effects on heme oxygenase-1 induction and antioxidant activities", European Journal of Pharmacology, vol. 635, 2010 (available online Mar. 9, 2010), pp. 16-22 (7 pages).
Weyemi et al., "SOD2 deficiency promotes aging phenotypes in mouse skin", Aging, vol. 4, No. 2, Feb. 2012, pp. 116-118 (3 pages).
Yang et al.,"Preparation of Chlorogenic acid derivatives as antitumor agents", Database Casreact, Chemical Abstract Service, Accession No. 164:88590, XP002765957, Dec. 9, 2015, 12 pages.
International Search Report (PCT/ISA/210) issued in PCT/EP2017/059898, dated Jun. 13, 2017.
Written Opinion (PCT/ISA/237) issued in PCT/EP2017/059898, dated Jun. 13, 2017.

* cited by examiner

AMIDE DERIVATIVES OF POLYCAFFEOYLQUINIC ACIDS, PROCESS FOR PRODUCING SAME AND USES THEREOF

FIELD OF INVENTION

The present invention relates to amide derivatives of poly-substituted quinic acids (abbreviated as "PSQ"), the method for producing same, uses thereof as medicinal product, notably for the treatment and/or prevention of inflammation, and pharmaceutical, cosmetic or nutraceutical compositions containing same.

PRIOR ART

Inflammation is a set of reactions generated by the body in response to an aggression.

Inflammation can be caused by physical aggression (such as hot, cold, ionizing radiation) or chemical aggression (by acidic or basic compounds, bacterial toxins). It can also be the result of infection (related to the presence in the body of living pathogenic organisms such as bacteria, viruses, parasites or fungi). It can also be caused by an immune reaction secondary to the reintroduction into the body of an antigen (allergy) such as an antibiotic. Finally, it is often the result of tissue necrosis, itself secondary to many causes, for example arterial occlusion.

The purpose of the inflammatory reaction is to defend the body, and inflammation, when visible, classically appears as four clinical signs: redness, pain, swelling and/or increased heat.

The inflammatory method progresses through three successive stages:
- a stage characterized by vascular-circulatory reactions;
- a stage characterized by cellular reactions (productive phase);
- a stage of healing or regeneration.

There are two types of inflammation: acute inflammation and chronic inflammation. Acute inflammation involves the elimination of the agent responsible for the inflammation and the repair of damaged tissue. Its signs are multiple: skin redness in burns, tonsil swelling in angina, joint inflammation in sprains, or coughing to eliminate pathogens in bronchitis. It can be reversed in a few minutes or days.

Chronic inflammation is an inflammation of prolonged duration, due to the persistence of one or more stressors, which the body can no longer spontaneously stop, and which can become harmful to the body. Predisposing factors are persistent aggression (such as gastric acid in peptic ulcer), inadequate host response to infection, chronic autoimmune disease (such as rheumatoid arthritis or ulcerative colitis). It is the inflammation and its consequences that become the disease itself, often serious and disabling. Each organ can be affected by this chronic inflammation: digestive tract (Crohn's disease), lungs (asthma), skin (psoriasis), nasal cavity mucosa (rhinitis), vessels (vascular accidents), nervous system (multiple sclerosis), joints (all rheumatism). A better understanding of chronic inflammation has also revealed its presence in situations where other mechanisms are involved: cancers, transplant immunity, age-related macular degeneration (AMD), etc.

Cells present in infected or damaged tissue, such as resident mononuclear phagocytes (macrophages and dendritic cells) and mast cells, are the first cells activated by danger signals. In response to this activation, they release active compounds called inflammation mediators, such as histamine, pro-inflammatory cytokines and leukotrienes or prostaglandins. The functional consequences of this activation are elimination of the pathogen (e.g. by phagocytosis) and/or repair of the Lesion (extracellular matrix remodelling).

Cytokines are small proteins secreted by cells in response to various stimuli. At the level of the immune response, they allow immune cells to direct the response according to the nature of the detected signal. Inflammation-mediating cytokines include interleukin-6 (IL-6), interleukin-8 (IL-8) and tumour necrosis factor α (TNFα).

IL-6 is produced by phagocytes (macrophages and dendritic cells) and endothelial cells in the event of inflammation. It induces local activation of phagocytes and modification of the endothelium. It promotes the recruitment of blood monocytes to tissues and the production of acute phase proteins by hepatocytes.

IL-8 (IL-8 or CX-CL8) is produced by epithelial cells following the detection of potentially pathogenic microbiological or chemical agents. Its main role is to ensure the recruitment of neutrophils at the infection site by creating a chemotactic gradient that guides phagocytic cells having corresponding surface receptors.

TNFα is produced by macrophages, resident dendritic cells and mast cells. TNFα stimulates the expression of adhesion molecules and the production of chemokines by endothelial cells allowing the recruitment of blood leukocytes (neutrophils, eosinophils, monocytes or NK lymphocytes) to the inflammatory source. TNFα also activates the microbicidal systems of phagocytes and is mitogenic for T and B lymphocytes (to induce the adaptive response if the innate response is insufficient to resolve the infection). Finally, TNFα activates the production of growth factors, which will be essential for the repair of damaged tissue.

Prostaglandins, notably prostaglandin E2 ($PGE_2$), and leukotrienes, notably leukotriene $B_4$ ($LTB_4$), are lipid mediators of inflammation and induce increased vessel dilation and permeability, facilitating the arrival of leukocytes at the inflammation site.

Certain caffeic acid derivatives, such as caffeic acid phenethyl ester (CAPE), are known to be important inhibitors of inflammation mediators, particularly $LTB_4$ (Fitzpatrick et al.). These derivatives are also known for their cytoprotective effect, notably via induction of haem oxygenase-1 (HO-1) production (Xinyu Wang et al.).

HO-1 plays a crucial role in cytoprotection against cellular oxidative stress. It is highly inducible by various stimuli that cause cellular stress. Since the enzyme limits the rate of haem metabolism, HO-1 exerts its protective effects by maintaining appropriate levels of cellular haem and the release of bioactive molecules, notably biliverdin, free iron and carbon monoxide. Biliverdin and its reduced form, bilirubin, are powerful antioxidants that can contribute to the beneficial effects of HO-1 (Barañano et al., 2002; Stocker et al., 1987.). Carbon monoxide effects mediation of HO-1 protection and has anti-inflammatory and anti-apoptotic effects (Otterbein et al., 2003).

Dicaffeoylquinic acids, particularly 3,4-O-dicaffeoylquinic acid and 4,5-O-dicaffeoylquinic acid, are also known in the art for their anti-inflammatory activity. These compounds are known to inhibit leukotriene $B_4$ ($LTB_4$) synthesis and IL-8 production (Gianfranco Peluso et al.).

3,4,5-Tricaffeoylquinic acid inhibits the production of inflammation mediators (particularly cytokines and chemokines) in keratinocytes treated with the lipopolysaccharide involved in inflammatory skin disease pathogenesis (Lee, S A et al.).

However, other derivatives of caffeic acid, such as methyl caffeate or chlorogenic acid, have been shown not to have a significant anti-inflammatory effect (Xinyu Wang et al.), demonstrating that small structural variations can abolish anti-inflammatory properties.

There is a need for novel compounds to inhibit inflammation mediators and to induce an even stronger cytoprotective effect than those described in the prior art.

EP 2 128 125 describes the antiviral effects of certain amide derivatives of dicaffeoylquinic acids and the use thereof, notably in the treatment of infection by HIV, hepatitis B virus and respiratory syncytial virus. The anti-inflammatory properties of these compounds have not been assessed.

Surprisingly, the inventors have shown that novel amide derivatives of PCQ not only have anti-inflammatory properties but that they are significantly superior to those of dicaffeoylquinic acids.

SUMMARY OF THE INVENTION

Surprisingly, the inventors discovered that certain amide derivatives of PSQ have remarkable anti-inflammatory effects and can be used in the treatment of inflammation. The inventors also discovered that amide derivatives of PSQ have a major cytoprotective potential, notably on cells in the inflammatory state.

In a first aspect, the present invention therefore relates to a compound amide derivative of PSQ or a mixture of compounds of general formula (IA):

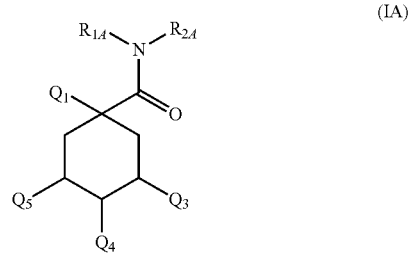

(IA)

wherein
$R_{1A}$ and $R_{2A}$ represent, independently of each other:
H, provided that $R_{1A}$ and $R_{2A}$ are not both a hydrogen atom,
a butyl group,
a $C_7$-$C_{30}$ alkyl group,
a $C_7$-$C_{30}$ alkylaryl or arylalkyl group, or
a $C_7$-$C_{18}$ aryl group;
and
$Q_1$, $Q_3$, $Q_4$ and $Q_5$ represent, independently of each other, an OH group, caffeoyl group, maloyl group, caffeoylmaloyl group or maloylcaffeoyl group, provided that at least one of these radicals is not an OH group,
or a pharmaceutically acceptable salt or stereoisomer or hydrate thereof.

In a second aspect, the invention relates to a method for producing a compound of the general formula (IA)

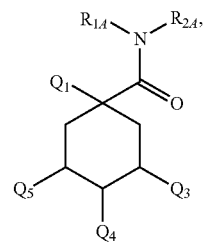

(IA)

wherein
$R_{1A}$ and $R_{2A}$ represent, independently of each other:
H, provided that $R_{1A}$ and $R_{2A}$ are not both a hydrogen atom,
a butyl group,
a $C_7$-$C_{30}$ alkyl group,
a $C_7$-$C_{30}$ alkylaryl or arylalkyl group, or
a $C_7$-$C_{18}$ aryl group;
and
$Q_1$, $Q_3$, $Q_4$ and $Q_5$ represent, independently of each other, an OH group, caffeoyl group, maloyl group, caffeoylmaloyl group or maloylcaffeoyl group, provided that at least one of these radicals is not an OH group,
or a pharmaceutically acceptable salt or stereoisomer or hydrate thereof,
characterized in that it comprises a step a) during which a poly-substituted quinic acid reacts with a compound of formula $HNR_{1A}R_{2A}$.

In a third aspect, the present invention relates to a compound obtainable by said method according to the invention.

In another aspect, the present invention relates to a compound or a mixture of compounds of general formula (IB):

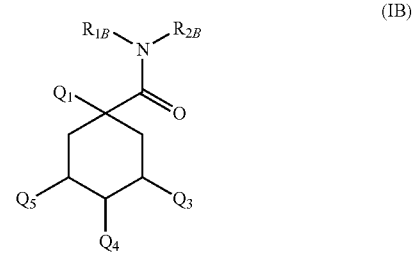

(IB)

wherein
$R_{1B}$ and $R_{2B}$ represent, independently of each other:
H,
a $C_1$-$C_{30}$ alkyl group,
a $C_7$-$C_{30}$ alkylaryl or arylalkyl group, or
a $C_6$-$C_{18}$ aryl group;
and
$Q_1$, $Q_3$, $Q_4$ and $Q_5$ represent, independently of each other, an OH group, caffeoyl group, maloyl group, caffeoylmaloyl group or maloylcaffeoyl group, provided that at least one of these radicals is not an OH group,
or a pharmaceutically acceptable salt or stereoisomer or hydrate thereof,
for use in the treatment and/or prevention of inflammation.

The present invention also relates to a compound or a mixture of compounds (amide derivative of PSQ) of general formula (IA):

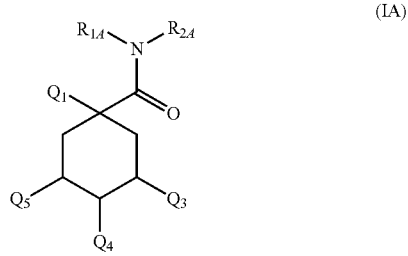

(IA)

wherein $R_{1A}$ and $R_{2A}$ represent, independently of each other:
  H, provided that $R_{1A}$ and $R_{2A}$ are not both a hydrogen atom,
  a butyl group,
  a $C_7$-$C_{30}$ alkyl group,
  a $C_7$-$C_{30}$ alkylaryl or arylalkyl group, or
  a $C_7$-$C_{18}$ aryl group;
and
$Q_1$, $Q_3$, $Q_4$ and $Q_5$ represent, independently of each other, an OH group, caffeoyl group, maloyl group, caffeoylmaloyl group or maloylcaffeoyl group, provided that at least one of these radicals is not an OH group,
or a pharmaceutically acceptable salt or stereoisomer or hydrate thereof,
for use as medicinal product.

DETAILED DESCRIPTION OF THE INVENTION

Definitions

Figure 1:
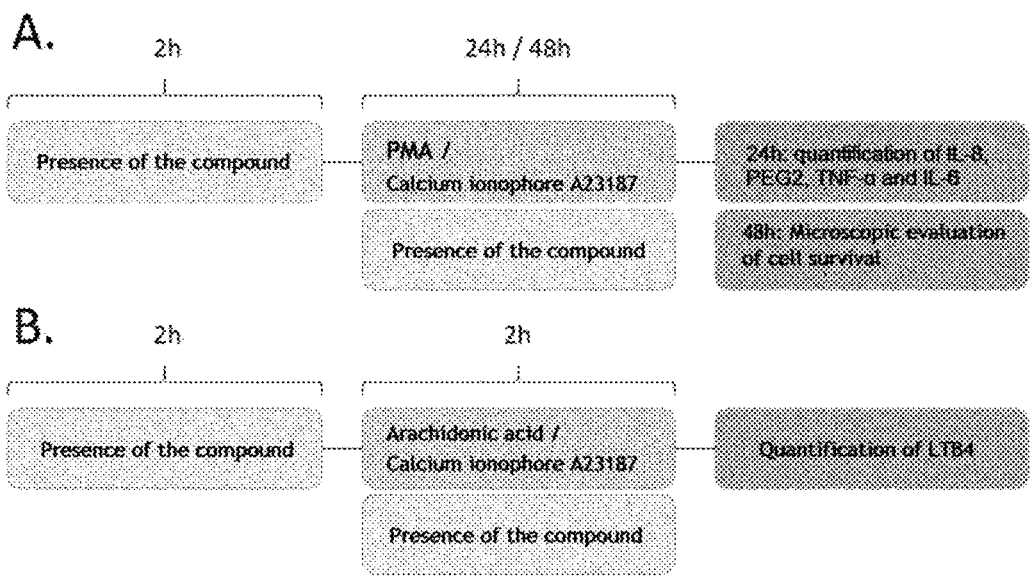
FIG. 1: Induction schemes for the various inflammatory mediators studied: A. Induction scheme for IL-8, PGE2, IL-6 and TNF-α; B. Induction scheme for LTB4.

In the context of the present invention, "$C_x$-$C_y$ alkyl group" means a cyclic or branched cyclic, linear or branched, saturated or unsaturated monovalent hydrocarbon chain having from x to y carbon atoms.

Therefore, in the context of the present invention, "$C_7$-$C_{30}$ alkyl" group means a cyclic or branched cyclic, linear or branched, saturated or unsaturated monovalent hydrocarbon chain having from 7 to 30 carbon atoms, preferably from 7 to 26 carbon atoms, more preferably from 7 to 24 carbon atoms, even more preferably from 7 to 22 carbon atoms, more particularly from 7 to 20 carbon atoms, especially from 7 to 18 carbon atoms. Non-exhaustive examples include heptyl, octyl, nonyl, decyl, undecyl, dodecyl, tridecyl, tetradecyl, pentadecyl, hexadecyl, heptadecyl, octadecyl, nonadecyl, eicosyl, docosyl, tetracosyl, hexacosyl, geranyl, farnesyl, geranylgeranyl, oleyl, citronellyl and squalenyl groups.

In a preferred embodiment of the invention, the alkyl groups are linear.

In the context of the present invention, $C_x$-$C_y$ aryl group means an aromatic hydrocarbon that adheres to Hückel's aromaticity rule, is mono- or polycyclic, and has from x to y carbon atoms.

Therefore, in the context of the present invention, "$C_x$-$C_y$ aryl" group means an aromatic hydrocarbon that adheres to Hückel's aromaticity rule, is mono- or polycyclic, and has from x to y carbon atoms. Examples include cyclooctatetraene, biphenyl, naphthalene, azulene, anthracene, phenanthrene, annulene-18 groups.

In the context of the present invention, $C_7$-$C_{30}$ alkylaryl group means a $C_1$-$C_{24}$ alkyl group covalently linked to a $C_6$-$C_{18}$ aryl group.

In the context of the present invention, $C_7$-$C_{30}$ arylalkyl group means a $C_6$-$C_{18}$ aryl group covalently linked to a $C_1$-$C_{24}$ alkyl group.

"Caffeoyl group" means a radical of general formula (VI), derived from caffeic acid:

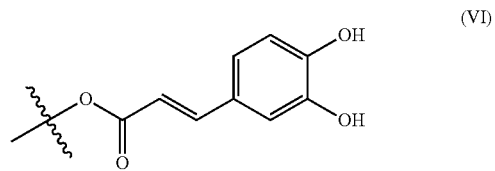

(VI)

"Maloyl group" means a radical of general formula (VIIa) or (VIIb), derived from malic acid:

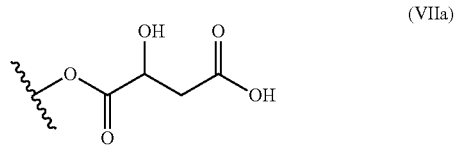

(VIIa)

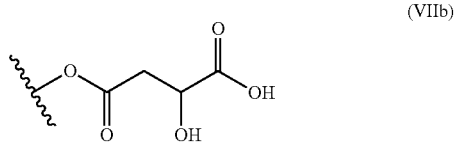

(VIIb)

"Caffeoylmaloyl group" means a radical of general formula (VIIIa) or (VIIIb):

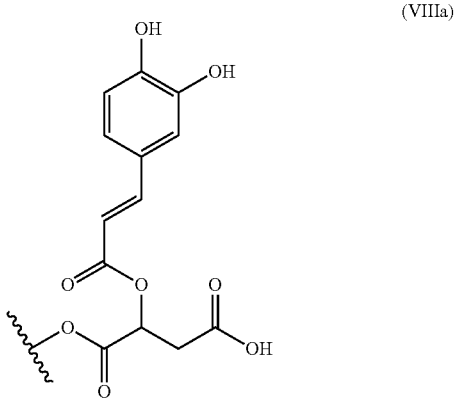

(VIIIa)

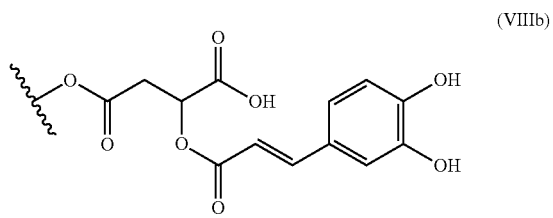

(VIIIb)

"Maloylcaffeoyl group" means a radical of general formula (IXa) or (IXb) or (IXc) or (IXd):

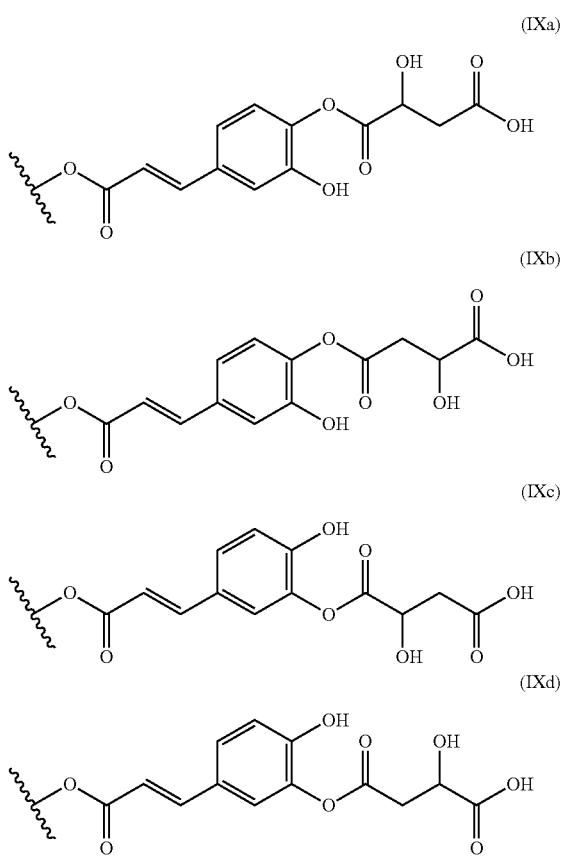

"Poly-substituted quinic acid" (abbreviated as "PSQ" throughout the present description) means a mono, di, tri or tetra ester composed of a quinic acid molecule of which one, two, three or all four alcohol functions have been esterified by a caffeic acid, a malic acid, or a mixture of caffeic acid and malic acid. PSQs are therefore acids of general formula (IV):

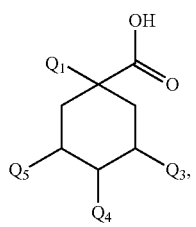

wherein $Q_1$, $Q_3$, $Q_4$ and $Q_5$ represent, independently of each other, an OH group, caffeoyl group, maloyl group, caffeoyl-maloyl group or maloylcaffeoyl group, provided that at least one of these radicals is not an OH group.

In a preferred embodiment of the invention, PSQ is a polycaffeoylquinic acid (abbreviated as "PCQ" throughout this description), corresponding to a mono, di, tri or tetra ester composed of a quinic acid molecule of which one, two, three or all four alcohol functions have been esterified by a caffeic acid. PCQs are therefore acids of general formula (IV) as defined above wherein $Q_1$, $Q_3$, $Q_4$ and $Q_5$ represent, independently of each other, an OH group or caffeoyl group, provided that at least one of these radicals is not an OH group.

The various isomers of PSQ are therefore acids of general formula (IV), with $Q_1$, $Q_3$, $Q_4$ and $Q_5$ as defined non-exhaustively in Tables 1 to 4 below.

TABLE 1

Examples of PSQ structure in which three of radicals $Q_1$, $Q_3$, $Q_4$ and $Q_5$ represent an OH group

| Acid name | $Q_1$ | $Q_3$ | $Q_4$ | $Q_5$ |
| --- | --- | --- | --- | --- |
| 1-O-Caffeoylquinic acid | Caffeoyl | OH | OH | OH |
| 3-O-Caffeoylquinic acid | OH | Caffeoyl | OH | OH |
| 4-O-Caffeoylquinic acid | OH | OH | Caffeoyl | OH |
| 5-O-Caffeoylquinic acid | OH | OH | OH | Caffeoyl |

TABLE 2

Examples of PSQ structure in which two of radicals $Q_1$, $Q_3$, $Q_4$ and $Q_5$ represent an OH group.

| Acid name | $Q_1$ | $Q_3$ | $Q_4$ | $Q_5$ |
| --- | --- | --- | --- | --- |
| 1,3-O-Dicaffeoylquinic (1,3-DCQ) | Caffeoyl | Caffeoyl | OH | OH |
| 1,4-O-Dicaffeoylquinic (1,4-DCQ) | Caffeoyl | OH | Caffeoyl | OH |
| 1,5-O-Dicaffeoylquinic (1,5-DCQ) | Caffeoyl | OH | OH | Caffeoyl |
| 3,4-O-Dicaffeoylquinic (3,4-DCQ) also called isochlorogenic acid B | OH | Caffeoyl | Caffeoyl | OH |
| 3,5-O-Dicaffeoylquinic (3,5-DCQ) also called isochlorogenic acid A | OH | Caffeoyl | OH | Caffeoyl |
| 4,5-O-Dicaffeoylquinic (4,5-DCQ) also called isochlorogenic acid C | OH | OH | Caffeoyl | Caffeoyl |

TABLE 3

Examples of PSQ structure in which one of radicals $Q_1$, $Q_3$, $Q_4$ and $Q_5$ represents an OH group.

| Acid name | $Q_1$ | $Q_3$ | $Q_4$ | $Q_5$ |
| --- | --- | --- | --- | --- |
| 1,3,4-O-Tricaffeoylquinic acid (1,3,4-TCQ) | Caffeoyl | Caffeoyl | Caffeoyl | OH |
| 1,3,5-O-Tricaffeoylquinic acid (1,3,5-TCQ) | Caffeoyl | Caffeoyl | OH | Caffeoyl |
| 1,4,5-O-Tricaffeoylquinic acid (1,4,5-TCQ) | Caffeoyl | OH | Caffeoyl | Caffeoyl |

TABLE 3-continued

Examples of PSQ structure in which one of radicals $Q_1$, $Q_3$, $Q_4$ and $Q_5$ represents an OH group.

| Acid name | $Q_1$ | $Q_3$ | $Q_4$ | $Q_5$ |
|---|---|---|---|---|
| 3,4,5-O-Tricaffeoylquinic acid (3,4,5-TCQ) | OH | Caffeoyl | Caffeoyl | Caffeoyl |
| 1-O-(2-O-Caffeoylmaloyl)-(3,5-O-dicaffeoyl)quinic acid | Caffeoylmaloyl | Caffeoyl | OH | Caffeoyl |
| 1-O-Maloyl-(3,4,5-O-tricaffeoyl)quinic acid | Maloyl | Caffeoyl | Caffeoyl | Caffeoyl |

TABLE 4

Example of PSQ structure in which none of radicals $Q_1$, $Q_3$, $Q_4$ and $Q_5$ represents an OH group

| Acid name | $Q_1$ | $Q_3$ | $Q_4$ | $Q_5$ |
|---|---|---|---|---|
| 1,3,4,5-O-Tetracaffeoylquinic acid (TetraCQ) | Caffeoyl | Caffeoyl | Caffeoyl | Caffeoyl |
| 1-O-(2-O-Caffeoylmaloyl)-(3,4,5-O-tricaffeoyl)quinic acid | Caffeoylmaloyl | Caffeoyl | Caffeoyl | Caffeoyl |

According to the present invention, "carboxyl group activator" means any reagent or combination of reagents capable of activating the carboxylic acid function to allow it to be coupled with a nucleophile under mild reaction conditions. Non-exhaustive examples include activators of the carbodiimide family such as dicyclohexylcarbodiimide (DCC), diisopropylcarbodiimide (DIC), N-ethyl-N(3-dimethylaminopropyl)carbodiimide (EDCI) alone or in combination with alcohols allowing the transient formation of activated esters such as, for example, 1-hydroxybenzotriazole (HOBT), 1-hydroxy-7-azabenzotriazole (HOAt), 1-hydroxysuccinimide (HOSu) or (hydroxyimino)cyanoacetate ethyl. The useful activator may also be part of the phosphonium, uronium and/or guanidinium salts family. Examples include benzotriazol-1-yloxy)tris(dimethylamino)phosphonium hexafluorophosphate (BOP), benzotriazol-1-yloxytripyrrolidinophosphonium hexafluorophosphate (PyBOP), (1-cyano-2-ethoxy-2-oxoethylidenaminooxy) dimethylamino-morpholino-carbenium hexafluorophosphate (COMU), N,N,N',N'-tetramethyl-O-(1H-benzotriazol-1-yl)uronium hexafluorophosphate (HBTU), (O-(6-chloro-1-hydrocibenzotriazol-1-yl)-1,1,3,3-tetramethyluronium tetrafluoroborate (TCTU), (2-(7-aza-1H-benzotriazole-1-yl)-1,1,3,3-tetramethyluronium hexafluorophosphate) (HATU).

More particularly, the carboxyl group activator is selected from diisopropylcarbodiimide (DIC) and 1-hydroxybenzotriazole (HOBT).

In the present invention, "pharmaceutically acceptable" means that which is useful in the preparation of a pharmaceutical composition that is generally safe, non-toxic and neither biologically nor otherwise undesirable and that is acceptable for both veterinary and human pharmaceutical use.

The expression "pharmaceutically acceptable salts" of a compound means salts that are pharmaceutically acceptable, as defined herein, and that have the desired pharmacological activity of the parent compound. Such salts include:

(1) hydrates and solvates, (2) pharmaceutically acceptable acid addition salts formed with pharmaceutically acceptable inorganic acids such as hydrochloric acid, hydrobromic acid, sulphuric acid, nitric acid, phosphoric acid and the like; or formed with pharmaceutically acceptable organic acids such as acetic acid, benzenesulphonic acid, benzoic acid, camphorsulphonic acid, citric acid, ethane-sulphonic acid, fumaric acid, glucoheptonic acid, gluconic acid, glutamic acid, glycolic acid, hydroxynaphthoic acid, 2-hydroxyethanesulphonic acid, lactic acid, maleic acid, malic acid, mandelic acid, methanesulphonic acid, muconic acid, 2-naphthalenesulphonic acid, propionic acid, salicylic acid, succinic acid, dibenzoyl-L-tartaric acid, tartaric acid, p-toluenesulphonic acid, trimethylacetic acid, trifluoroacetic acid and the like, or (3) pharmaceutically acceptable base addition salts formed when an acidic proton present in the parent compound is either replaced by a metal ion, for example an alkali metal ion, an alkaline earth metal ion or an aluminium ion; or coordinated with a pharmaceutically acceptable organic or inorganic base. Acceptable organic bases include diethanolamine, ethanolamine, N-methylglucamine, triethanolamine, tromethamine and the like. Acceptable inorganic bases include aluminium hydroxide, calcium hydroxide, potassium hydroxide, sodium carbonate and sodium hydroxide.

In the context of the present invention, "inflammation" means a set of reactions generated by the body in response to an aggression. The clinical signs of these reactions include redness, pain, swelling and/or increased heat, and biological signs include the recruitment of immune system cells and the release of inflammation mediators such as pro-inflammatory cytokines, leukotrienes or prostaglandins.

Similarly, "inflammatory disease" means a disease resulting from excessive and often chronic inflammation. These include inflammatory diseases resulting from an excessive specific immune system response, such as asthma, psoriasis, rhinitis, arthrosis and autoimmune diseases including Raynaud's syndrome, autoimmune thyroiditis, dermatitis, multiple sclerosis, rheumatoid arthritis, insulin-dependent diabetes mellitus, uveitis, inflammatory bowel diseases (notably Crohn's disease and ulcerative colitis), systemic lupus erythematosus; and diseases resulting from an excessive non-specific immune system response, such as diseases due to adult respiratory distress syndrome, septic shock, oxygen toxicity, multiple organ dysfunction syndrome secondary to sepsis, multiple organ dysfunction syndrome secondary to trauma, tissue reperfusion injury due to extracorporeal circulation, myocardial infarction, acute glomerulonephritis, vasculitis, reactive arthritis, dermatosis with acute inflammatory components, stroke, thermal injury, haemodialysis, cytapheresis, necrotizing enterocolitis and a granulocyte transfusion associated syndrome.

Amide Derivatives of Poly-Substituted Quinic Acids (PSQ)

The present invention therefore relates to compounds or a mixture of compounds, amide derivatives of PSQ, of general formula (IA):

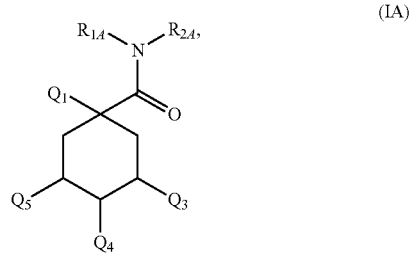

(IA)

wherein
$R_{1A}$ and $R_{2A}$ represent, independently of each other:
  H, provided that $R_{1A}$ and $R_{2A}$ are not both a hydrogen atom,
  a butyl group,
  a $C_7$-$C_{30}$ alkyl group,
  a $C_7$-$C_{30}$ alkylaryl or arylalkyl group, or
  a $C_7$-$C_{18}$ aryl group;
and
$Q_1$, $Q_3$, $Q_4$ and $Q_5$ represent, independently of each other, an OH group, caffeoyl group, maloyl group, caffeoylmaloyl group or maloylcaffeoyl group, provided that at least one of these radicals is not an OH group;
or a pharmaceutically acceptable salt or stereoisomer or hydrate thereof.

In particular, the present invention relates to compounds or a mixture of compounds, amide derivatives of PCQ, of general formula (IA) as defined above wherein $Q_1$, $Q_3$, $Q_4$ and $Q_5$ represent, independently of each other, an OH group or caffeoyl group, provided that at least one of these radicals is not an OH group.

Preferably, the present invention relates to compounds or a mixture of compounds, amide derivatives of PCQ, of general formula (IA) as defined above wherein any two of radicals $Q_1$, $Q_3$, $Q_4$ and $Q_5$ represent a caffeoyl group, the other two representing an OH group.

Among the compounds of formula (IA) according to the present invention, mention may be made of the amide derivatives of:
5-O-caffeoylquinic acid ($Q_1$=$Q_3$=$Q_4$=OH);
1,3-O-dicaffeoylquinic acid ($Q_4$=$Q_5$=OH);
1,4-O-dicaffeoylquinic acid ($Q_3$=$Q_5$=OH);
1,5-O-dicaffeoylquinic acid ($Q_3$=$Q_4$=OH);
3,4-O-dicaffeoylquinic acid ($Q_1$=$Q_5$=OH), this amide derivative corresponds to isochlorogenamide B;
3,5-O-dicaffeoylquinic acid ($Q_1$=$Q_4$=OH), this amide derivative corresponds to isochlorogenamide A;
4,5-O-dicaffeoylquinic acid ($Q_1$=$Q_3$=OH), this amide derivative corresponds to isochlorogenamide C;
1,3,4-O-tricaffeoylquinic acid ($Q_5$=OH);
1,3,5-O-tricaffeoylquinic acid ($Q_4$=OH);
1,4,5-O-tricaffeoylquinic acid ($Q_3$=OH);
3,4,5-O-tricaffeoylquinic acid ($Q_1$=OH); and
1,3,4,5-O-tetracaffeoylquinic acid.

In particular, among the advantageous compounds of formula (IA) of the present invention, mention may be made of the amide derivatives of:
1,3-O-dicaffeoylquinic acid ($Q_4$=$Q_5$=OH);
1,4-O-dicaffeoylquinic acid ($Q_3$=$Q_5$=OH);
1,5-O-dicaffeoylquinic acid ($Q_3$=$Q_4$=OH);
3,4-O-dicaffeoylquinic acid ($Q_1$=$Q_5$=OH), this amide derivative corresponds to isochlorogenamide B;
3,5-O-dicaffeoylquinic acid ($Q_1$=$Q_4$=OH), this amide derivative corresponds to isochlorogenamide A; and
4,5-O-dicaffeoylquinic acid ($Q_1$=$Q_3$=OH), this amide derivative corresponds to isochlorogenamide C.

Advantageously, the compounds of general formula (IA) according to the invention are characterized in that $Q_1$ represents an OH group. Thus, among the advantageous compounds of the present invention mention may be made of the amide derivatives of:
3,4-O-dicaffeoylquinic acid ($Q_1$=$Q_5$=OH), this amide derivative corresponds to isochlorogenamide B;
3,5-O-dicaffeoylquinic acid ($Q_1$=$Q_4$=OH), this amide derivative corresponds to isochlorogenamide A; and
4,5-O-dicaffeoylquinic acid ($Q_1$=$Q_3$=OH), this amide derivative corresponds to isochlorogenamide C.

The particularly advantageous compounds of general formula (IA) according to the invention are those characterized in that $Q_1$ and $Q_4$ represent an OH group and $Q_3$ and $Q_5$ represent a caffeoyl group, thus corresponding to the amide derivatives of 3,5-O-dicaffeoylquinic acid (3,5-DCQ).

In an advantageous embodiment, the amide derivatives of PSQ, notably the amide derivatives of PCQ, according to the invention are characterized in that $R_{1A}$ is a hydrogen atom. In a particular embodiment $R_{1A}$ is a hydrogen atom and $R_{2A}$ is a butyl group or an advantageously linear $C_7$-$C_{30}$, in particular $C_7$-$C_{26}$, preferably $C_7$-$C_{24}$, preferentially $C_7$-$C_{22}$, more preferentially $C_7$-$C_{20}$, in particular $C_7$-$C_{18}$, alkyl group, notably an alkyl group selected from heptyl, octyl, nonyl, decyl, undecyl, dodecyl, tridecyl, tetradecyl, pentadecyl, hexadecyl, heptadecyl, octadecyl, nonadecyl, eicosyl, docosyl, tetracosyl, hexacosyl, geranyl, farnesyl, geranylgeranyl, oleyl, citronellyl and squalenyl groups, preferably an alkyl group selected from octyl, dodecyl or octadecyl groups.

In another embodiment, the amide derivatives of PSQ, notably the amide derivatives of PCQ, according to the invention are characterized in that $R_{1A}$ is a hydrogen atom and $R_{2A}$ is a $C_7$-$C_{10}$ aryl group, in particular a naphthyl, or a $C_7$-$C_{30}$ arylalkyl group, in particular a phenyl-($C_1$-$C_{24}$) alkyl, more particularly a phenylbutyl.

Preferably, the compounds according to the invention are of general formula (II) or (III):

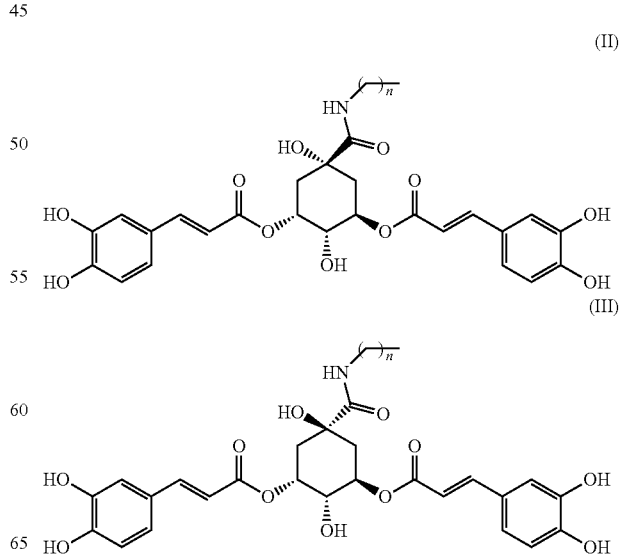

wherein n is equal to 3 or is greater than or equal to 6, in particular, n is equal to 3, 7, 11 or 17.

Method for Producing a Compound According to the Invention and Compound Obtainable by Said Method There exist in the art methods for producing amide derivatives of PCQ known to the skilled person. These compounds are generally produced by chemical synthesis from quinic acid and caffeic acid.

An exemplary method for producing amide derivatives of PCQ is described in European patent application EP 2 128 125, notably in schemes 1 and 2. In that document, quinic acid is first subjected to an acid-catalysed protection reaction of its carboxyl and hydroxyl groups. The quinide obtained is treated with an amine to promote conversion of the carboxyl group at position 1 into an amide group. The hydroxyl groups of the resulting amide derivative of quinic acid are then deprotected by an acid-catalysed deprotection reaction. The amide derivatives of PCQ are finally obtained by acylation of the hydroxyl groups of the amide derivatives of quinic acid with allyl-caffeic acid chloride then by a deprotection reaction of the allyl groups in the presence of Rh(PPh$_3$)$_3$Cl/DABCO/EtOH or Pd(PPH$_3$)$_4$/morpholine/THF.

This type of method for synthesizing amide derivatives of PCQ produces a mixture of isochlorogenamides A, B and C. To obtain a single regioisomer of amide derivative of PCQ, such as isochlorogenamide A (amide derivatives of 3,5-DCQ) alone, an additional purification step is required. Such a purification step is difficult to carry out given the structural similarities and results in a significantly lower yield.

The inventors discovered that the production of amide derivatives of PSQ could be carried out in one step by hemisynthesis from a particular PSQ making it possible to obtain amide derivatives of this PSQ in the form of a single regioisomer.

In particular, the inventors discovered that isochlorogenamide A could be obtained by reacting 3,5-DCQ acid with an amine.

In a second aspect, the present invention also relates to a method for producing a compound of general formula (IA)

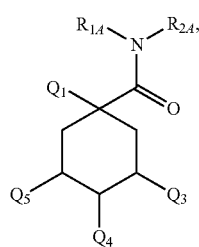

(IA)

wherein $R_{1A}$, $R_{2A}$, $Q_1$, $Q_3$, $Q_4$ and $Q_5$ are as defined above; or a pharmaceutically acceptable salt or stereoisomer or hydrate thereof,
characterized in that it comprises a step a) during which a PSQ reacts with a compound of formula HNR$_{1A}$R$_{2A}$. In particular, said PSQ is a PCQ, advantageously selected from 3-O-caffeoylquinic acid, 3,5-DCQ, 3,4-DCQ, 4,5-DCQ, 3,4,5-TCQ and TetraCQ, advantageously the PCQ is 3,5-DCQ, 3,4-DCQ, 4,5-DCQ, more advantageously the PCQ is 3,5-DCQ.

Advantageously, Q$_1$, Q$_3$, Q$_4$ and Q$_5$ represent, independently of each other, an OH group or caffeoyl group, provided that at least one of these radicals is not an OH group. In particular, any two of radicals Q$_1$, Q$_3$, Q$_4$ and Q$_5$ represent a caffeoyl group, the other two representing an OH group.

More particularly, the present invention relates to a method for producing a compound of general formula (IA), wherein $R_{1A}$ is a hydrogen atom, more particularly $R_{1A}$ is a hydrogen atom and $R_{2A}$ is a butyl group or an advantageously linear $C_7$-$C_{30}$, in particular $C_7$-$C_{26}$, more particularly of $C_7$-$C_{24}$, preferably $C_7$-$C_{22}$, preferentially $C_7$-$C_{20}$, in particular $C_7$-$C_{18}$, alkyl group, notably an alkyl group selected from heptyl, octyl, nonyl, decyl, undecyl, dodecyl, tridecyl, tetradecyl, pentadecyl, hexadecyl, heptadecyl, octadecyl, nonadecyl, eicosyl, docosyl, tetracosyl, hexacosyl, geranyl, farnesyl, geranylgeranyl, oleyl, citronellyl and squalenyl groups, preferably an alkyl group selected from octyl, dodecyl or octadecyl groups; or a $C_7$-$C_{18}$ aryl group, notably an aryl group selected from cyclooctatetraene, biphenyl, naphthalene, azulene, anthracene, phenanthrene, annulene-18 groups.

Advantageously, the compound of formula HNR$_{1A}$R$_{5A}$ is selected from alkylamines, notably butan-1-amine or $C_7$-$C_{30}$, in particular $C_7$-$C_{26}$, more particularly $C_7$-$C_{24}$, even more particularly $C_7$-$C_{20}$, preferably $C_7$-$C_{18}$, alkylamines.

More particularly, the compound of formula HNR$_{1A}$R$_{2A}$ is selected from one of the following compounds: octan-1-amine, laurylamine, 1-octadecylamine, 4-phenylbutan-1-amine or 2-naphthylamine.

In a preferred embodiment, the present invention relates to a method for producing a compound of general formula (II) or (III):

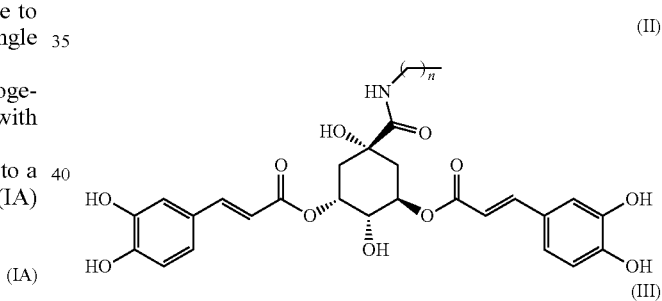

(II)

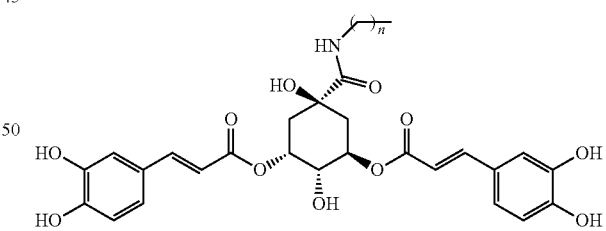

(III)

wherein n is an integer equal to 3 or between 6 and 29, in particular equal to 3 or between 6 and 25, preferably n is equal to 3, 7, 11 or 17,
characterized in that it comprises a step a) during which a 3,5-DCQ reacts with a compound of general formula (V)

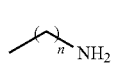

(V)

wherein n is as defined above.

In another preferred embodiment, the present invention relates to a method for producing one of the following compounds of respective formulae (IIa), (IIb), (IIc) and (IId):

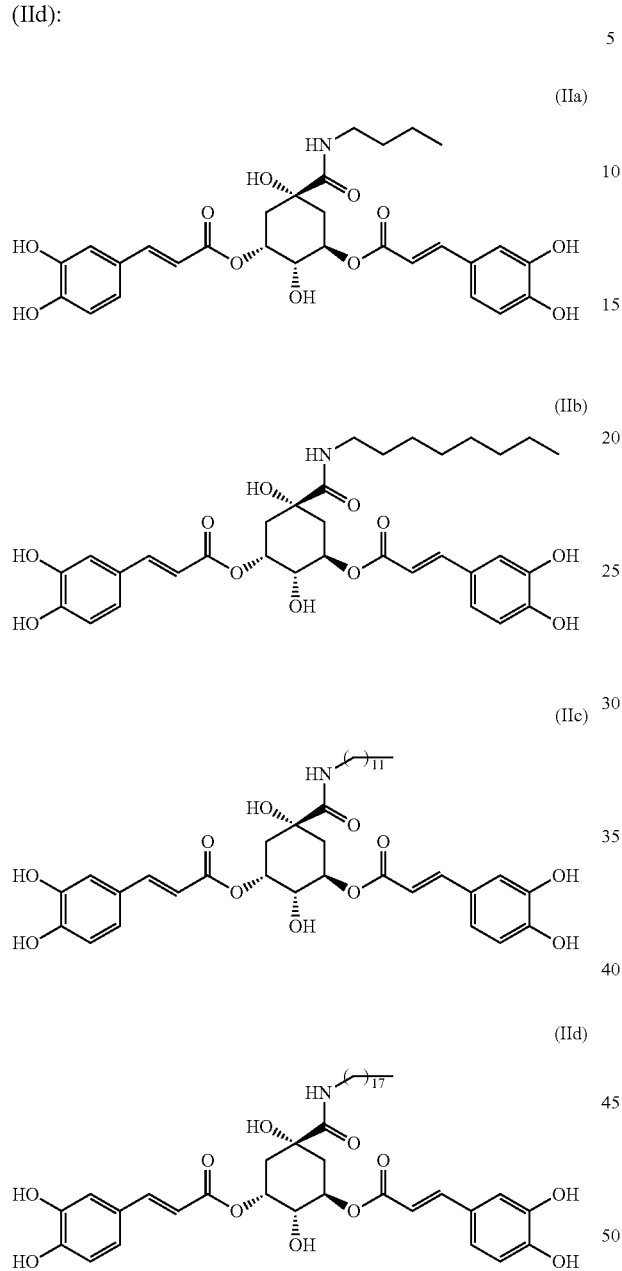

Advantageously, the reaction of step a) is carried out in the presence of an inert solvent such as dichloromethane, N,N-dimethylformamide or tetrahydrofuran, notably at a temperature between −15° C. and the reflux temperature of the solvent.

In an embodiment of the invention, step a) of the method according to the invention is optionally preceded by a step of activating the carboxyl group of a PSQ, notably PCQ, notably with a carboxyl group activator, such as 1-(3-dimethylaminopropyl)-3-ethylcarbodiimide in combination with 1-hydroxybenzotriazole hydrate.

The methods according to the invention can, for example, be described by the following schemes 1 and 2:

Scheme 1. Hemisynthesis of isochlorogenamide derivatives from PSQ

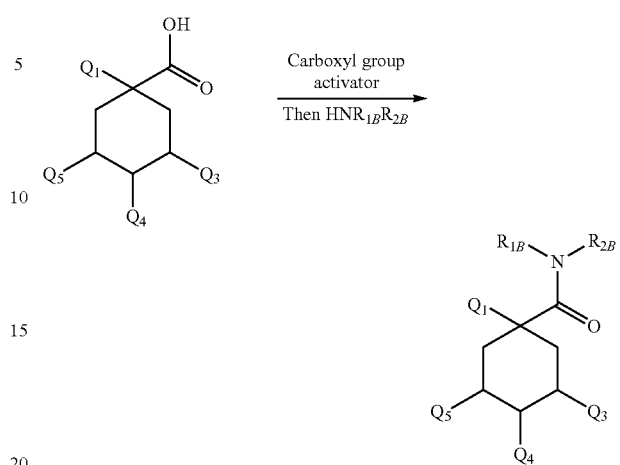

Scheme 2. Hemisynthesis of isochlorogenamide derivatives from PSQ

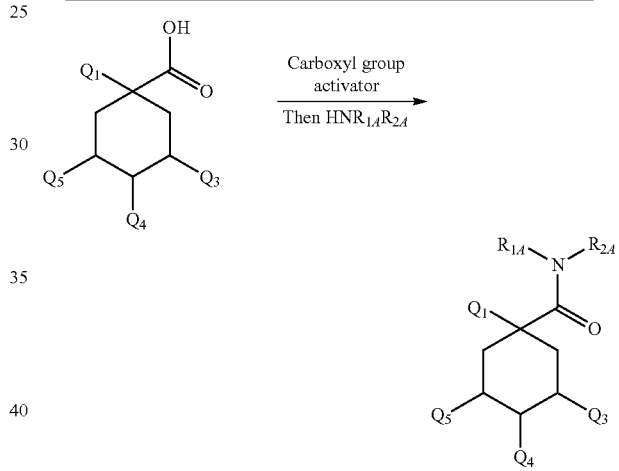

The methods for preparing compounds according to the invention may optionally include additional protection and/or deprotection steps to avoid secondary reactions well known to the skilled person, or to avoid the formation of several regioisomers of the compounds according to the invention.

The compounds obtained by the methods according to the invention may also be purified by methods known to the skilled person. Examples include methods of purification by crystallization, chromatography or extraction.

The invention also relates to a compound obtainable by the methods according to the invention, as described above.

Therapeutic Applications

The inventors discovered that the compounds according to the invention have anti-inflammatory properties.

In the context of the present invention, the compounds according to the invention can be used in the treatment of inflammation or inflammatory diseases, notably inflammatory diseases resulting from an excessive specific immune system response, such as asthma, psoriasis, rhinitis, arthrosis and autoimmune diseases including Raynaud's syndrome, autoimmune thyroiditis, dermatitis, multiple sclerosis, rheumatoid arthritis, insulin-dependent diabetes mellitus, uveitis, inflammatory bowel diseases (including Crohn's disease and ulcerative colitis), systemic lupus erythematosus; and diseases resulting from an excessive non-specific immune system response, such as diseases due to adult respiratory distress syndrome, septic shock, oxygen toxicity, multiple organ dysfunction syndrome secondary to sepsis, multiple organ dysfunction syndrome secondary to trauma, tissue reperfusion injury due to extracorporeal circulation, myocardial infarction, acute glomerulonephritis, vasculitis, reactive arthritis, dermatosis with acute inflammatory components, stroke, thermal injury, haemodialysis, cytapheresis, necrotizing enterocolitis and a granulocyte transfusion associated syndrome.

In the context of the present invention, the origin of the inflammation may be physical (heat, cold, ionizing radiation, infrared, solar radiation), mechanical (abrasion), chemical (contact with irritants or allergens) or biological (microbe, fungus), or the inflammation may be due to oxidative stress.

In another aspect, the invention therefore relates to a compound or a mixture of compounds of general formula (IB),

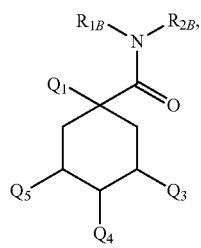

(IB)

wherein $R_{1B}$, $R_{2B}$, R, $Q_1$, $Q_3$, $Q_4$ and $Q_5$ are as defined above, or a pharmaceutically acceptable salt or stereoisomer or hydrate thereof, for use for preventing and/or treating inflammation or inflammatory disease.

According to another aspect, the invention also relates to a compound or a mixture of compounds of general formula (IB) according to the invention for use for preventing and/or treating any of the inflammatory diseases mentioned above.

Furthermore, the invention relates to the use of a compound or a mixture of compounds of general formula (IB) according to the invention for the manufacture of a drug for preventing and/or treating inflammation or inflammatory disease, notably one of the diseases mentioned above.

The invention also relates to a method for preventing or treating inflammation or inflammatory disease, notably one of the diseases mentioned above, comprising administering a therapeutically effective amount of at least one compound of formula (IB) according to the invention to a patient in need thereof.

In another embodiment, the invention relates to a compound or a mixture of compounds of general formula (IA)

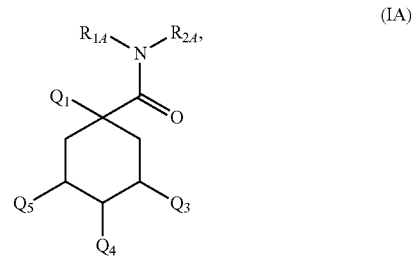

(IA)

wherein $R_{1A}$, $R_{2A}$, R, $Q_1$, $Q_3$, $Q_4$ and $Q_5$ are as defined above,
or a pharmaceutically acceptable salt or stereoisomer or hydrate thereof,
for use as a drug.

The invention also relates to a compound or a mixture of compounds of formula (IA) according to the invention for use as a drug for preventing and/or treating inflammation or inflammatory disease, notably one of the diseases mentioned above.

The present invention notably relates to a compound or a mixture of compounds of formula (IA) according to the invention for use as a drug for preventing and/or treating psoriasis.

Furthermore, the invention relates to the use of a compound or a mixture of compounds of general formula (IA) according to the invention for the manufacture of a drug, notably for preventing and/or treating inflammation or inflammatory disease, in particular one of the diseases mentioned above. The invention notably relates to the use of a compound or a mixture of compounds of general formula (IA) according to the invention for the manufacture of a drug for the preventing and/or treating psoriasis.

The invention also relates to a method for preventing or treating, notably inflammation or inflammatory disease, in particular one of the diseases mentioned above, comprising administering a therapeutically effective amount of at least one compound of formula (IA) according to the invention to a patient in need thereof. The invention notably relates to a method for preventing and/or treating psoriasis, comprising administering a therapeutically effective amount of at least one compound of formula (IA) according to the invention to a patient in need thereof.

Cosmetic or Pharmaceutical Compositions

The present invention also relates to a cosmetic or pharmaceutical composition comprising as active agent at least one compound according to the invention or an extract according to the invention and advantageously a cosmetically or pharmaceutically acceptable excipient.

The optimal modes of administration, dosages and dosage forms of the pharmaceutical or cosmetic compositions according to the invention may be determined according to the criteria generally taken into account in establishing a pharmaceutical or cosmetic treatment adapted to a subject, such as the age or body weight of the patient, the seriousness of his or her general condition, tolerance to the treatment, the side effects observed, the skin type. Depending on the type of administration desired, the pharmaceutical or cosmetic composition according to the invention may further comprise at least one pharmaceutically or cosmetically acceptable excipient. The cosmetic or pharmaceutical composition according to the present invention may further comprise at least one adjuvant pharmaceutically or cosmetically known to the skilled person, selected from thickeners, preservatives, fragrances, dyes, chemical or mineral filters, moisturizing agents, geothermal water, etc.

Advantageously, the cosmetic or pharmaceutical composition comprises at least one compound of general formula (IA) according to the invention in an amount between 0.01 and 10%, in particular between 0.05 and 5%, more particularly between 0.1 and 2%, by weight, based on the total weight of the composition.

Pharmaceutical Compositions

The present invention also relates to a pharmaceutical composition comprising as active agent at least one compound of general formula (IA)

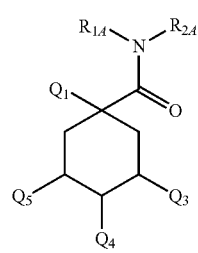

(IA)

wherein $R_{1A}$, $R_{2A}$, R, $Q_1$, $Q_3$, $Q_4$ and $Q_5$ are as defined above,
or a pharmaceutically acceptable salt or stereoisomer or hydrate thereof,
and advantageously a pharmaceutically acceptable excipient.

The pharmaceutical composition is particularly suitable for oral, nasal, transdermal, parenteral, topical, rectal, and mucosal administration. It can be in dry form, such as a soft capsule, hard capsule, tablet, lyophilisate, powder, granule, or patch, or in liquid form, such as a solution, suspension, spray, cream or gel.

The pharmaceutically acceptable excipient is known to the skilled person and is selected according to the mode of administration of the pharmaceutical composition. By way of example, the pharmaceutically acceptable excipient may be selected from the group consisting of diluents, binders, disintegrants, dyes, lubricants, solubilizers, absorption promoters, film-forming agents, gelling agents, and mixtures thereof.

The pharmaceutical composition according to the invention may further comprise at least one compound selected from the group consisting of emollients, moisturizing active agents, keratin synthesis activators, keratin regulators, keratolytics, skin barrier restructuring agents (skin lipid synthesis activators, peroxisome proliferator-activated receptor (PPAR) agonists), keratinocyte differentiation activators (retinoids, Calcidone□, calcium), antibiotics, antibacterials, antifungals, antivirals, sebum regulators, immunomodulators such as tacrolimus, pimecrolimus, oxazolines, preservatives, anti-irritant agents, soothing agents, sunblocks and sunscreens, antioxidants, growth factors, healing agents or eutrophic molecules, medicinal products and anti-inflammatory agents.

The present invention also relates to a pharmaceutical composition according to the invention, for use for preventing and/or treating inflammation, notably skin inflammation. The present invention also relates to a pharmaceutical composition according to the invention, for use as a drug for preventing and/or treating psoriasis.

The present invention also relates to the use of a pharmaceutical composition according to the invention, to produce a drug intended for preventing and/or treating inflammation, notably skin inflammation. The invention notably relates to the use of a pharmaceutical composition according to the invention, for the manufacture of a drug for preventing and/or treating psoriasis.

Furthermore, the invention relates to a method for treating and/or preventing inflammation, notably skin inflammation, in a subject in need thereof, comprising administering to the subject a therapeutically effective amount of a pharmaceutical composition according to the invention. The invention notably relates to a method for preventing and/or treating psoriasis, comprising administering a therapeutically effective amount of a pharmaceutical composition according to the invention to a patient in need thereof.

The present invention also relates to a pharmaceutical composition according to the invention, for use in preventing or slowing skin ageing, in healing the skin and/or in promoting regeneration of dermal tissues.

The present invention also relates to the use of a pharmaceutical composition according to the invention, for the manufacture of a drug intended to prevent or slow skin ageing, to heal the skin and/or to promote regeneration of dermal tissues.

Furthermore, the invention relates to a method for preventing or slowing skin ageing, for healing the skin and/or for promoting regeneration of dermal tissues, in a subject in need thereof, comprising administering to the subject a therapeutically effective amount of a pharmaceutical composition according to the invention.

Cosmetic Compositions

The present invention therefore relates to a cosmetic composition comprising as active agent at least one compound according to the invention or an extract according to the invention and advantageously a cosmetically acceptable excipient.

The cosmetic composition according to the invention may further comprise other cosmetically active agents, such as other anti-ageing agents; or moisturizing agents; agents with calming, soothing or relaxing activity; agents that stimulate skin microcirculation; sebum regulators for the care of oily skin; cleansing or purifying agents; anti-radical agents; anti-inflammatory agents; chemical or mineral sunblocks, etc.

The cosmetically acceptable excipient may be selected from polymers, silicone compounds, surfactants, rheology agents, humectants, penetrants, oily components, waxes, emulsifiers, film-forming agents, fragrances, electrolytes, pH adjusters, antioxidants, preservatives, dyes, pearlescents, pigments and mixtures thereof.

The cosmetic composition according to the invention is advantageously intended for topical application. It may be in cream, milk, lotion, gel, serum, spray, foam, solution, ointment, emulsion, patch or mask form.

The invention also relates to the use as active agent of a compound of formula (IB) or formula (IA) according to the invention, in a cosmetic composition or to produce a cosmetic composition, for treating or preventing skin ageing, skin inflammation (calming or soothing effect), and/or for promoting healing and regeneration of dermal tissues.

The cosmetic composition according to the invention may notably be intended to prevent or slow skin ageing.

The cosmetic composition according to the invention may notably be intended to prevent or treat skin inflammation.

The cosmetic composition according to the invention may notably be intended to produce a calming effect or a soothing effect on the skin.

The cosmetic composition according to the invention may notably be intended to promote healing.

The cosmetic composition according to the invention may notably be intended to promote regeneration of dermal tissues.

The invention also relates to a cosmetic skin care method aimed at preventing or treating skin ageing and/or skin inflammation, characterized in that it comprises applying a cosmetic composition according to the invention to at least part of the skin of the body or face.

The invention also relates to a cosmetic skin care method for producing a calming effect or a soothing effect on the skin and/or for promoting regeneration of dermal tissues, characterized in that it comprises applying a cosmetic composition according to the invention to at least part of the skin of the body or face.

Advantageously, in the method according to the invention, the cosmetic composition is applied to a subject in need thereof, notably in anticipation of or following a single or repeated exposure of the skin to oxidative stress. Indeed, the latter can generate an excess of free radicals that can accelerate the signs of skin ageing. Also, the fight against various pathologies or pro-inflammatory conditions also generates reactive oxygen species.

The following examples are intended to illustrate the present invention.

EXAMPLES

Example 1: Hemisynthesis of Amide Derivatives of 3,5-DCQ from 3,5-DCQ (Isochlorogenic Acid A)

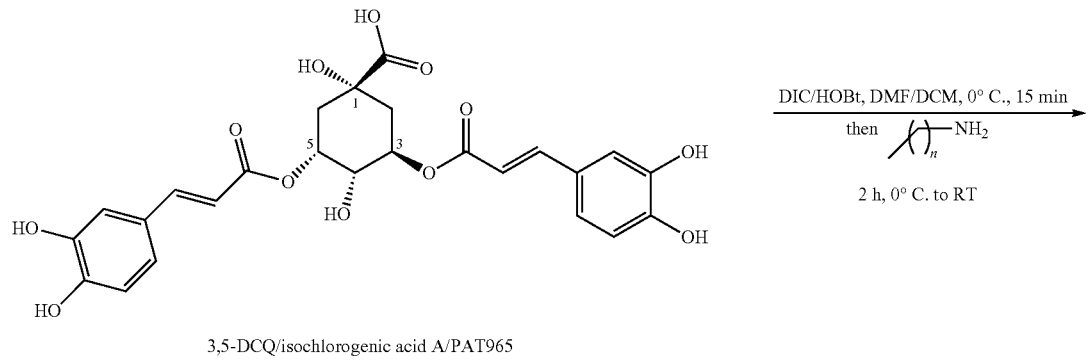

Scheme 2. Hemisynthesis of amide derivatives of 3,5-DCQ from 3,5-DCQ 3,5-DCQ/isochlorogenic acid A/PAT965

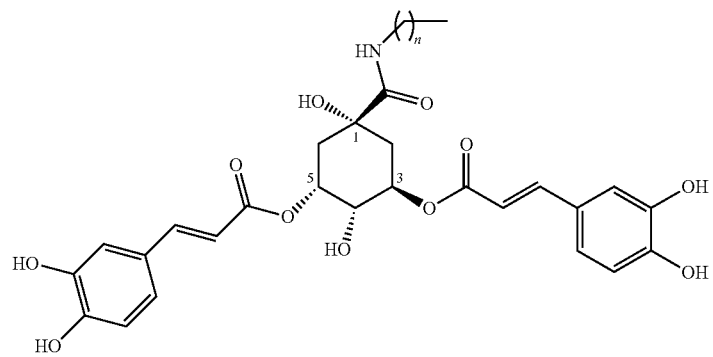

Amide derivatives oF 3,5-DCQ

Synthesis of octyl-isochlorogenamide A (2E,2'E)-((1R,2S,3R,5S)-2,5-dihydroxy-5-(octylcarbamoyl)cyclohexane-1,3-diyl) bis(3-(3,4-dihydroxyphenyl)acrylate)=PAT1657

To a solution of 3,5-DCQ (300 mg; 0.581 mmol) and 1-hydroxybenzotriazole hydrate (118 mg; 0.871 mmol) in anhydrous N,N-dimethylformamide (2249 µL; 29.0 mmol) and dichloromethane (2243 µL; 35.9 mmol) is added dropwise 1-(3-dimethylaminopropyl)-3-ethylcarbodiimide (123 µL, 0.697 mmol) at a temperature of 0° C.

The reaction mixture is stirred for 15 minutes at 0° C. and then a solution of octan-1-amine (241 µL, 1.452 mmol) in anhydrous dichloromethane (1000 µL, 15.54 mmol) is added over 45 minutes.

The reaction mixture is stirred for 1 hour at 0° C. then for 2 hours at room temperature. The reaction is then stopped by adding a 1M aqueous HCl solution (30 mL). The organic phase is then extracted with 3 times 30 mL of EtOAc and washed with 50 mL of 1M HCl solution and brine (50 mL), dried over $MgSO_4$, filtered and evaporated under vacuum to obtain a solid.

The solid obtained is purified by preparative HPLC (Vydac Denali C18 column, 50×250 mm, 10 µm) with a solvent A ($H_2O$+0.1% HCOOH) and a solvent B (MeOH) with a linear gradient from 80 to 100% of B for 15 minutes at a flow rate of 60 mL/minute. The compound obtained is a white solid.

Isolated yield: 49% (180 mg);
Molecular formula: $C_{33}H_{41}NO_{11}$;
Molecular weight: 627.68 g/mol;
$^1H$ (400 MHz, $CD_3OD$, 300K) δ(ppm) 0.87 (t, J=6.3 Hz, 3H), 1.17-1.37 (m, 10H), 1.49 (t, J=6.5 Hz, 2H), 1.98-2.20 (m, 3H), 2.31 (dd, J=15.1 Hz, 3.3 Hz, 1H), 3.17 (m, 2H), 3.92 (dd, J=9.7 Hz, 3.3 Hz, 1H), 5.46 (m, 1H), 5.52 (m, 1H), 6.30 (d, J=15.8 Hz, 1H), 6.37 (d, J=15.8 Hz, 1H), 6.77 (d, J=1.0 Hz, 1H), 6.79 (d, J=1.0 Hz, 1H), 6.90-7.00 (m, 2H), 7.05 (m, 1H), 7.07 (m, 1H), 7.60 (d, J=15.8 Hz, 1H), 7.62 (d, J=15.8 Hz, 1H). $^{13}C$ (100 MHz, $CD_3OD$, 300K) δ(ppm) 14.6, 23.8, 28.0, 30.5 (2×), 30.6, 33.1, 36.9, 39.7, 40.6, 71.8, 72.8, 73.9, 76.7, 115.3 (×2), 115.4, 115.8, 116.6 (2×), 123.1 (2×), 127.9, 128.1, 146.9, 147.0, 147.2, 147.3, 149.6, 149.8, 169.1 (2×), 177.8.
Rf (EtOAc/Cy 8/2+1% AcOH)=0.22
LC/MS analyses were performed on a Zorbax Eclipse column ($C_{18}$, 3.0×100 mm, 1.8 µm) with a solvent A ($H_2O$+0.1% HCOOH) and a solvent B (acetonitrile) as eluent with a linear gradient from 5 to 95% of B for 15 minutes, a linear gradient from 95% to 100% for 1 minute then an isocratic mode at 100% of B for 2 minutes at a flow rate of 0.4 mL/min. Rt=12.161 min, m/z (ESI+APCI Negative mode) [M-H]⁻ 626.3 (100).

Synthesis of butyl-isochlorogenamide A (2E,2'E)-((1R,2S,3R,5S)-5-(butylcarbamoyl)-2,5-dihydroxycyclohexane-1,3-diyl) bis(3-(3,4-dihydroxyphenyl)acrylate)=PAT1658

Butyl-isochlorogenamide A is produced as previously described using butan-1-amine as starting amine.

The solid obtained is purified by preparative HPLC (Vydac Denali C18 column, 50×250 mm, 10 µm) with a solvent A ($H_2O$+0.1% HCOOH) and a solvent B (MeOH) with an isocratic mode of 60% of B for 20 minutes at a flow rate of 60 mL/minute. The compound obtained is a white solid.

Isolated yield: 45% (148 mg);
Molecular formula $C_{29}H_{33}NO_{11}$;
Molecular weight: 571.57 g/mol;
$^1H$ (400 MHz, $CD_3OD$, 300K) δ(ppm) 0.90 (t, J=7.3 Hz, 3H), 1.32 (m, 2H), 1.37 (m, 2H), 2.05 (m, 2H), 2.16 (m, 1H), 2.31 (dd, J=3.2 Hz, 15.4 Hz, 1H), 3.18 (t, J=7.1 Hz, 2H), 3.93 (dd, J=3.3 Hz, 9.72 Hz, 1H), 5.46 (m, 1H), 5.53 (m, 1H), 6.30 (d, J=15.9 Hz, 1H), 6.37 (d, J=16 Hz, 1H), 6.77 (d, J=1.0 Hz, 1H), 6.79 (d, J=1.0 Hz, 1H), 6.92-6.99 (m, 2H), 7.05 (m, 1H), 7.07 (m, 1H), 7.60 (d, J=15.9 Hz, 1H), 7.62 (d, J=15.9 Hz, 1H). $^{13}C$ (100 MHz, $CD_3OD$, 300K) δ(ppm) 14.2, 21.1, 32.7, 36.9, 39.7, 40.3, 71.8, 72.8, 73.9, 76.7, 115.3 (×2), 115.4, 115.8, 116.6 (2×), 123.1 (2×), 127.9, 128.1, 146.9, 147.0, 147.2, 147.3, 149.6, 149.7, 169.1 (2×), 177.8.
Rf (EtOAc/Cy 8/2+1% AcOH)=0.15
LC/MS analyses were performed on a Zorbax Eclipse column ($C_{18}$, 3.0×100 mm, 1.8 µm) with a solvent A ($H_2O$+0.1% HCOOH) and a solvent B (acetonitrile) with a linear gradient from 5 to 95% of B for 15 minutes, a linear gradient from 95% to 100% for 1 minute then an isocratic mode at 100% of B for 2 minutes at a flow rate of 0.4 mL/min. Rt=9.579 min, m/z (ESI+APCI Negative mode) [M-H]⁻ 570.2 (100).

Synthesis of lauryl-isochlorogenamide A (2E,2'E)-((1R,2S,3R,5S)-5-(dodecylcarbamoyl)-2,5-dihydroxycyclohexane-1,3-diyl) bis(3-(3,4-dihydroxyphenyl) acrylate)=PAT1648

Lauryl-isochlorogenamide A is produced as previously described using laurylamine as starting amine.

The solid obtained is purified by HPLC (Luna $C_{18}$ Column, 5 µm, 21.2×250 mm) with a solvent A ($H_2O$+0.1% HCOOH) and a solvent B (acetonitrile) with an isocratic mode of 72% of B for 20 minutes at a flow rate of 20 mL/minute. The compound obtained is a white solid.

Isolated yield: 25% (101 mg);
Molecular formula $C_{37}H_{49}NO_{11}$;
Molecular weight: 683.79 g/mol;
$^1H$ (400 MHz, $CD_3OD$, 300K) δ(ppm) 0.88 (t, J=6.3 Hz, 3H), 1.05-1.38 (m, 18H), 1.49 (m, 2H), 1.98-2.20 (m, 3H), 2.31 (dd, J=15.1 Hz, 3.3 Hz, 1H), 3.17 (m, 2H), 3.92 (dd, J=9.7 Hz, 3.3 Hz, 1H), 5.46 (m, 1H), 5.52 (m, 1H), 6.30 (d, J=15.8 Hz, 1H), 6.37 (d, J=15.8 Hz, 1H), 6.77 (d, J=1.0 Hz, 1H), 6.79 (d, J=1.0 Hz, 1H), 6.90-7.00 (m, 2H), 7.05 (m, 1H), 7.07 (m, 1H), 7.60 (d, J=15.8 Hz, 1H), 7.62 (d, J=15.8 Hz, 1H). $^{13}C$ (100 MHz, $CD_3OD$, 300K) δ(ppm) 14.6, 23.9, 28.0, 30.5 (2×), 30.6 (2×), 30.8, 30.9 (2×), 33.2, 36.9, 39.7, 40.5, 71.8, 72.8, 73.9, 76.7, 115.3 (×2), 115.4, 115.9, 116.6 (2×), 123.1 (2×), 127.9, 128.1, 146.9, 147.0, 147.2, 147.2, 149.7, 149.8, 169.1 (2×), 177.8.
Rf (EtOAc/Cy 8/2+1% AcOH)=0.27
LC/MS analyses were performed on a Zorbax Eclipse column ($C_{18}$, 3.0×100 mm, 1.8 µm) with a solvent A ($H_2O$+0.1% HCOOH) and a solvent B (acetonitrile) with a linear gradient from 5 to 95% of B for 15 minutes, a linear gradient from 95% to 100% for 1 minute then an isocratic mode at 100% of B for 2 minutes at a flow rate of 0.4 mL/min. Rt=14.770 min, m/z (ESI+APCI Negative mode) [M-H]⁻ 682.3 (100).

Synthesis of octadecyl-isochlorogenamide A (2E,2'E)-((1R,2S,3R,5S)-2,5-dihydroxy-5-(octadecylcarbamoyl)cyclohexane-1,3-diyl) bis(3-(3,4-dihydroxyphenyl)acrylate)=PAT1656

Octadecyl-isochlorogenamide A is produced as previously described using 1-octadecylamine as starting amine.

The solid obtained is dissolved in 20 mL of a mixture of MeOH/DCM (1/1 v/v) and 3 g of Dowex 50WX8-100 is added. The reaction mixture is stirred for 30 minutes then filtered. The filtrate is evaporated under vacuum and the product obtained is purified by HPLC (Luna $C_{18}$ Column, 5 µm, 21.2×250 mm) with a solvent A ($H_2O$+0.1% HCOOH) and a solvent B (acetonitrile) with an isocratic mode of 96% of B for 5 minutes then an isocratic mode of 100% of B for 20 minutes at a flow rate of 20 mL/minute. The compound obtained is a white solid.

Isolated yield: 44% (195 mg);
Molecular formula $C_{43}H_{61}NO_{11}$;
Molecular weight: 767.94 g/mol;
$^1$H (250 MHz, $CD_3OD$, 300K) δ(ppm) 0.89 (t, J=6.3 Hz, 3H), 1.14-1.40 (m, 30H), 1.49 (m, 2H), 1.98-2.20 (m, 3H), 2.31 (dd, J=15.1 Hz, 3.3 Hz, 1H), 3.17 (m, 2H), 3.92 (dd, J=9.7 Hz, 3.3 Hz, 1H), 5.46 (m, 1H), 5.52 (m, 1H), 6.30 (d, J=15.8 Hz, 1H), 6.37 (d, J=15.8 Hz, 1H), 6.77 (d, J=1.0 Hz, 1H), 6.79 (d, J=1.0 Hz, 1H), 6.90-7.00 (m, 2H), 7.05 (m, 1H), 7.07 (m, 1H), 7.60 (d, J=15.8 Hz, 1H), 7.62 (d, J=15.8 Hz, 1H). $^{13}$C (67 MHz, $CD_3OD$, 300K) δ(ppm) 14.6, 23.9, 28.0, 30.5 (2×), 30.6 (2×), 30.8, 30.9 (8×), 33.2, 37.0, 39.7, 40.6, 71.8, 72.8, 73.9, 76.8, 115.3 (×2), 115.4, 115.9, 116.6 (2×), 123.1 (2×), 127.9, 128.1, 147.0 (2×), 147.2, 147.3, 149.7, 149.8, 169.1 (2×), 177.7.

Rf (EtOAc/Cy 8/2+1% AcOH)=0.27
LC/MS analyses were performed on a Zorbax Eclipse column ($C_{18}$, 3.0×100 mm, 1.8 µm) with a solvent A ($H_2O$+0.1% HCOOH) and a solvent B (acetonitrile) with a linear gradient from 5 to 95% of B for 15 minutes, a linear gradient from 95% to 100% for 1 minute then an isocratic mode at 100% of B for 9 minutes at a flow rate of 0.4 mL/min. Rt=19.020 min, m/z (ESI+APCI Negative mode) [M-H]$^-$ 766.4 (100).

Synthesis of phenylbutyl-isochlorogenamide A: (2E,2'E)-((1R,2S,3R,5S)-2,5-dihydroxy-5-(4-phenyl-butylcarbamoyl)cyclohexane-1,3-diyl) bis(3-(3,4-dihydroxyphenyl)acrylate)=PAT1961

Phenylbutyl-isochlorogenamide A is produced as previously described using 4-phenylbutan-1-amine as starting amine.

The solid obtained is purified by preparative HPLC (Luna C18 column, 21.5×250 mm, 5 µm) with a solvent A ($H_2O$+0.1% HCOOH) and a solvent B (MeOH) with an isocratic mode of 70% of B for 20 minutes at a flow rate of 15 mL/minute. The compound obtained is a white solid.

Isolated yield: 28% (17.43 mg);
Molecular formula $C_{35}H_{37}NO_{11}$;
Molecular weight: 647.66 g/mol;
$^1$H NMR (200 MHz, MeOD, 300K) δ (ppm) 1.42-1.77 (m, 4H), 1.91-2.41 (m, 4H), 2.51-2.67 (m, 2H), 3.22 (s, 2H), 3.93 (dd, J=9.5, 3.0 Hz, 1H), 5.38-5.66 (m, 2H), 6.36 (dd, J=15.8, 11.1 Hz, 2H), 6.80 (d, J=8.4 Hz, 2H), 6.99 (d, J=8.4 Hz, 2H), 7.37-7.03 (m, 7H), 7.64 (d, J=15.8 Hz, 2H).

Rf (EtOAc/Cy 8/2+1% AcOH)=0.38
LC/MS analyses were performed on a Poroshell 120 column ($C_{18}$, 3.0×150 mm, 2.7 µm) with a solvent A ($H_2O$+0.1% HCOOH) and a solvent B (acetonitrile) with a linear gradient from 5 to 95% of B for 15 minutes, a linear gradient from 95% to 100% for 1 minute then an isocratic mode at 100% of B for 10 minutes at a flow rate of 0.4 mL/min. Rt=11.995 min, m/z (ESI+APCI Negative mode) [M-H]$^-$ 646.2

Synthesis of 2-naphthyl-isochlorogenamide A: (2E,2'E)-((1R,2S,3R,5S)-2,5-dihydroxy-5-(naphthalen-2-ylcarbamoyl)cyclohexane-1,3-diyl) bis(3-(3,4-dihydroxyphenyl)acrylate)=PAT1960

2-Naphthyl-isochlorogenamide A is produced as previously described using 2-naphthylamine as starting amine.

The solid obtained is purified by preparative HPLC (Luna C18 column, 21.5×250 mm, 5 µm) with a solvent A ($H_2O$+0.1% HCOOH) and a solvent B (MeOH) with an isocratic mode of 70% of B for 20 minutes at a flow rate of 15 mL/minute. The compound obtained is a white solid.

Isolated yield: 34% (21.09 mg);
Molecular formula $C_{35}H_{31}NO_{11}$;
Molecular weight: 641.62 g/mol;
$^1$H (200 MHz, MeOD, 300K) δ (ppm) 1.95-2.56 (m, 4H), 4.02 (d, J=5.9 Hz, 1H), 5.48-5.64 (m, 2H), 6.36 (dd, J=24.4, 15.9 Hz, 2H), 6.65-7.17 (m, 6H), 7.26-7.46 (m, 2H), 7.50-7.89 (m, 6H), 8.23 (s, 1H).

Rf (EtOAc/Cy 8/2+1% AcOH)=0.52
LC/MS analyses were performed on a Poroshell 120 column ($C_{18}$, 3.0×150 mm, 2.7 µm) with a solvent A ($H_2O$+0.1% HCOOH) and a solvent B (acetonitrile) with a linear gradient from 5 to 95% of B for 15 minutes, a linear gradient from 95% to 100% for 1 minute then an isocratic mode at 100% of B for 10 minutes at a flow rate of 0.4 mL/min. Rt=12.272 min, m/z (ESI+APCI Negative mode) [M-H]$^-$ 640.2

Synthesis of octyl-chlorogenamide: (E)-((1R,2R,3R,5S)-2,3,5-trihydroxy-5-(octylcarbamoyl)cyclohexyl) 3-(3,4-dihydroxyphenyl)acrylate=PAT1962

Octyl-chlorogenamide is produced as previously described using 1-octylamine as starting amine and 3-chlorogenic acid as starting acid.

The solid obtained is purified by preparative HPLC (Luna C18 column, 21.5×250 mm, 5 µm) with a solvent A ($H_2O$+0.1% HCOOH) and a solvent B (MeOH) with an isocratic mode of 70% of B for 20 minutes at a flow rate of 15 mL/minute. The compound obtained is a white solid.

Isolated yield: 16% (14.99 mg);
Molecular formula $C_{24}H_{35}NO_8$;
Molecular weight: 465.53 g/mol;
$^1$H NMR (200 MHz, MeOD, 300K) δ (ppm) 0.78-1.04 (m, 3H), 1.15-1.42 (m, 10H), 1.43-1.59 (m, 2H), 1.84-2.24 (m, 4H), 3.08-3.27 (m, 2H), 3.73 (dd, J=9.8, 3.0 Hz, 1H), 4.25 (d, J=3.0 Hz, 1H), 5.30-5.54 (m, 1H), 6.31 (d, J=15.9 Hz, 1H), 6.80 (d, J=8.2 Hz, 1H), 6.97 (dd, J=8.2, 1.9 Hz, 1H), 7.07 (d, J=1.9 Hz, 1H), 7.60 (d, J=15.9 Hz, 1H).

Rf (EtOAc/Cy 8/2+1% AcOH)=0.28
LC/MS analyses were performed on a Poroshell 120 column ($C_{18}$, 3.0×150 mm, 2.7 µm) with a solvent A ($H_2O$+0.1% HCOOH) and a solvent B (acetonitrile) with a linear gradient from 5 to 95% of B for 15 minutes, a linear gradient from 95% to 100% for 1 minute then an isocratic mode at 100% of B for 10 minutes at a flow rate of 0.4 mL/min. Rt=12.762 min, m/z (ESI+APCI Negative mode) [M-H]$^-$ 464.2

Example 2: Analysis of the Effects of the Compounds According to the Invention on the Production of Inflammatory Mediators IL-6, IL-8, TNF-α, Leukotriene $B_4$ and Prostaglandin $E_2$ by NHEKs in the Inflammatory State The study consisted in measuring the anti-inflammatory effects of 6 compounds by analysis of the production of target inflammatory mediators: interleukin 8 (IL-8), prostaglandin E2 (PGE2), interleukin 6 (IL-6), tumour necrosis factor alpha (TNF-α) and leukotriene B4 (LTB4).

Materials and Methods

Compounds

The 6 compounds studied are described in Table 5 below:

TABLE 5

Compounds studied

| Code | Compound | Concentrations tested | Solvent |
|---|---|---|---|
| PAT965 | 3,5-DCQ (isochlorogenic acid A) | 100 μM, 50 μM, 25 μM, 12.5 μM, 6.25 μM | Compounds prepared in 100% DMSO |
| PAT964 | 3,4-DCQ (isochlorogenic acid B) | | |
| PAT967 | 4,5-DCQ (isochlorogenic acid C) | | |
| PAT1658 | Butyl-isochlorogenamide A | | |
| PAT1657 | Octyl-isochlorogenamide A | | |
| PAT1648 | Lauryl-isochlorogenamide A | | |

Cell Culture

The study was carried out on Normal Human Epidermal Keratinocytes (NHEKs) (Lonza, CC-2507, origin: foreskin) in monolayer culture in Epilife medium (Invitrogen, M-EPI-500-A) containing the components of the Human Keratinocyte Growth Supplement (HKGS) mixture (Invitrogen, S-001-K) added separately, except hydrocortisone having anti-inflammatory properties.

Determination of the Analytical Concentrations of the 6 Compounds by a Cytotoxicity Study To determine the optimal analytical concentration for each of the compounds, a preliminary experiment was performed on NHEKs. The study consisted in evaluating cell viability with MTS (3-(4,5-dimethythiazol-2-yl)-5-(3-carboxy-methoxyphenyl)-2-(4-sulphophenyl)-2H-tetrazolium) (Promega, G3581) after 26 h and 50 h of treatment with these compounds, at 5 concentrations (100 μM, 50 μM, 50 μM, 25 μM, 12.5 μM, 6.25 μM), in triplicate cultures (n=3). Cells were seeded in 24-well plate, 24 h before treatment at the various concentrations of the compounds to be tested.

0.008% SDS (VWR, 444464T) was used as positive control for cytotoxicity to validate the experiment.

Induction of the Inflammatory State in an NHEK Culture and Application of Compounds Induction of the Inflammatory State and Experimental Kinetics For the quantification of IL-8 and PGE2, the inflammatory state of the NHEKs in culture was induced by treatment with PMA (phorbol myristate acetate/10 ng/ml/H$_2$O) for 24 h. Induction of IL-6 was achieved by treatment with PMA (10 ng/ml/H$_2$O) combined with calcium ionophore A23187 (2 μM/DMSO) in medium containing calcium at a concentration of 0.8 mM. TNF-α secretion was induced by a combination of PMA (10 ng/ml/H$_2$O) and calcium ionophore A23187 (2 μM/DMSO) applied for 24 h (TNF-α) in medium containing 0.06 mM calcium. The reference molecules used are dexamethasone (10 μM/H$_2$O) and indomethacin (10 μg/ml/ethanol).

The induction of LTB4 production having a very fast kinetics, the scheme was adapted. In this case, the inflammatory state was induced for 2 h by applying arachidonic acid (a.a./1 μM/ethanol) combined with calcium ionophore A23187 (2 μM/DMSO). Nordihydroguaiaretic acid (NDGA) was used as reference molecule (2 μM/ethanol).

The effect of the compounds was studied by applying them to the keratinocyte culture medium 2 h prior to induction of the inflammatory state as well as during induction (2 h for LTB4, 24 h for IL-8, PGE2, IL-6 and TNF-α).

Each condition was carried out in triplicate cultures and the supernatants were recovered at the end of the various treatments.

The induction schemes for the various inflammatory mediators studied are shown in FIG. 1.

Culture supernatants were collected at the end of each kinetics studied. They were aliquoted and frozen at −20° C. until the day of analysis.

Quantification of the various inflammatory mediators was carried out with specific kits, based on a standard curve, according to the instructions provided by the kits' suppliers, R&D Systems and Cayman Chemical.

The cells, treated and not treated by the compounds to be tested, were observed under an optical microscope 48 h after the following inflammatory treatment: 10 ng/mL PMA/H$_2$O+2 μM calcium ionophore A23187/DMSO.

Result

Determination of the Analytical Concentration of Each of the 6 Compounds by a Cytotoxicity Study To optimize the working concentrations of the compounds, a cytotoxicity study on NHEKs was performed, on the basis of 5 concentrations (100 μM, 50 μM, 25 μM, 12.5 μM, 6.25 μM) of each of the 6 compounds prepared in DMSO.

The experimental parameters were identical to those used subsequently for the study of effects on inflammatory mediators, in terms of cell culture passages, confluence and contact time (26 h for IL-6, IL-8, TNF-α, LTB4 and PGE2).

0.008% SDS was used as positive control for cytotoxicity to validate the experiment.

Figure 2:
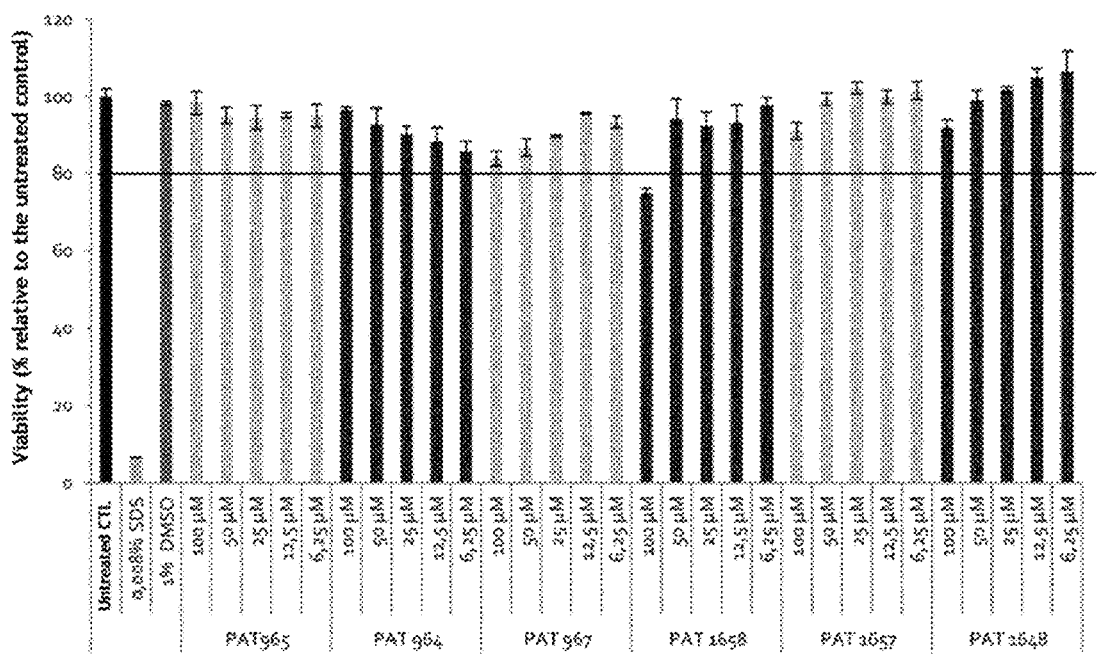
FIG. 2: Measurements of NHEK viability after 26 h of treatment with various concentrations of compounds PAT965, PAT964, PAT967, PAT1658, PAT1657 or PAT1648. Viability percentages were calculated relative to the untreated negative control (untreated CTL) set at 100% and to the positive control for cytotoxicity (0.008% SDS). 1% DMSO: vehicle control for the PAT compounds. The error bar corresponds to the standard deviation around the mean.
Figure 3:
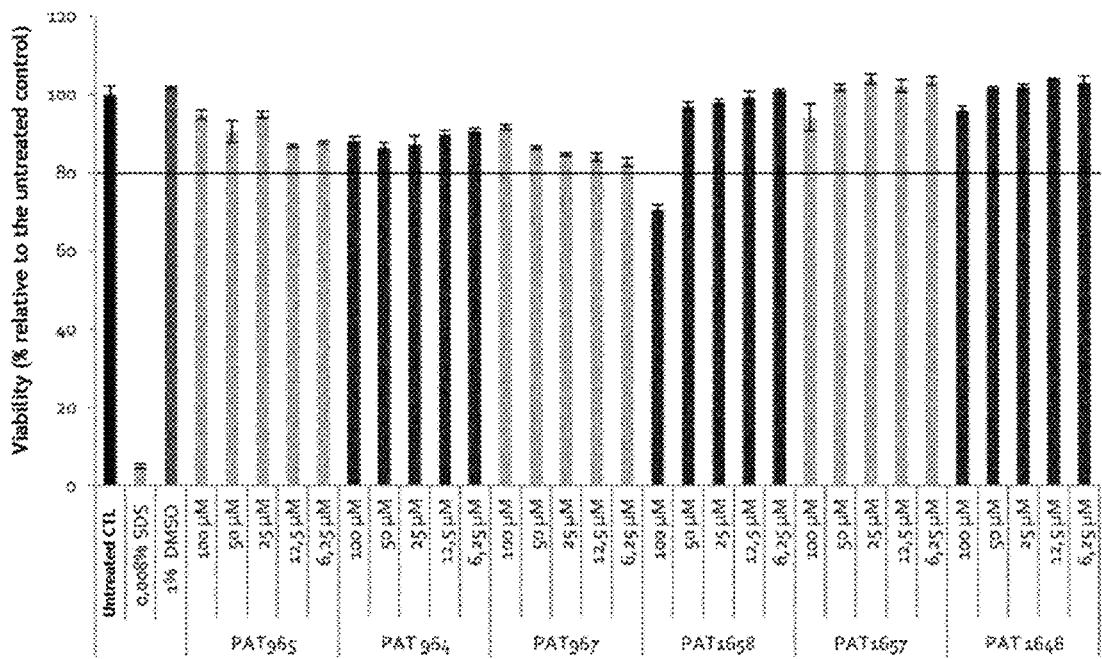
FIG. 3: Measurements of NHEK viability after 50 h of treatment with various concentrations of compounds PAT965, PAT964, PAT967, PAT1658, PAT1657 or PAT1648. Viability percentages were calculated relative to the untreated negative control (untreated CTL) set at 100% and to the positive control for cytotoxicity (0.008% SDS). 1% DMSO: vehicle control for the PAT compounds. The error bar corresponds to the standard deviation around the mean.

The results are illustrated in FIGS. 2 and 3 and are expressed as a percentage of the "untreated control (CTL)" condition and the cytotoxicity threshold was arbitrarily set at 80% viability.

Based on these results, a concentration of 50 μM was chosen for each of the 6 compounds.

Quantification of Mediators Secreted in Culture Supernatants by Keratinocytes in the Inflammatory State Before induction of the inflammatory state, the NHEKs were treated with the compounds and reference molecules for 2 h. The inflammatory state was then induced according to the conditions described in the methodology section, the culture supernatants were collected, and the various inflammatory mediators were quantified by the ELISA technique.

Quantification of IL-8

Figure 4:
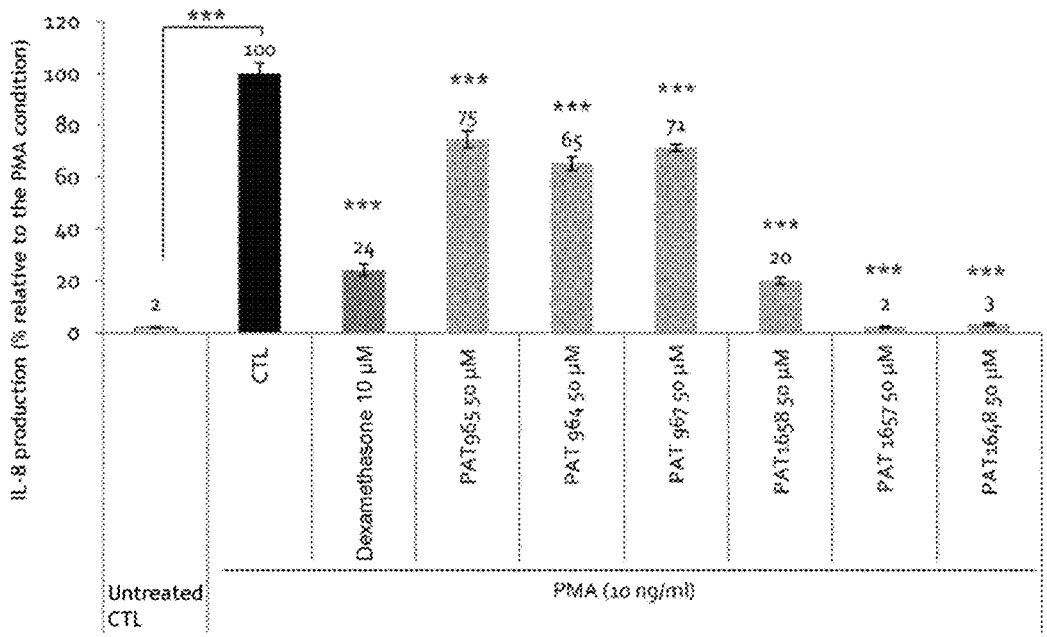
FIG. 4: Quantification of IL-8 production by NHEKs in the inflammatory state treated with compounds PAT965, PAT964, PAT967, PAT1658, PAT1657 or PAT1648. The results are expressed as a percentage of the condition treated with PMA (CTL) set at 100%. The graph shows the mean of the IL-8 measurements in supernatants from 3 independent cultures, as well as the standard deviation. P-values below 0.001 are considered very highly significant (***) (analysis of variance (ANOVA) and Dunnett comparison test against the PMA induced condition). Dexamethasone was used as reference molecule.

The effect of the compounds on IL-8 production is shown in FIG. 4. The data are expressed relative to IL-8 production by keratinocytes in the inflammatory state (treated with PMA), whose condition was arbitrarily set at 100%.

The results show that PMA treatment does induce IL-8 overproduction and 10 μM dexamethasone has a very highly significant inhibitory effect on IL-8 production, which validates the experiment.

Furthermore, each of the 6 compounds reduces, in a very highly significant manner, IL-8 production relative to the induced control condition (CTL). Compounds PAT1657 and PAT1648 are particularly effective, indeed superior to the reference molecule (dexamethasone), since they inhibit/reduce IL-8 production to the baseline level measured in the non-induced condition (untreated CTL).

Quantification of PGE2

Figure 5:
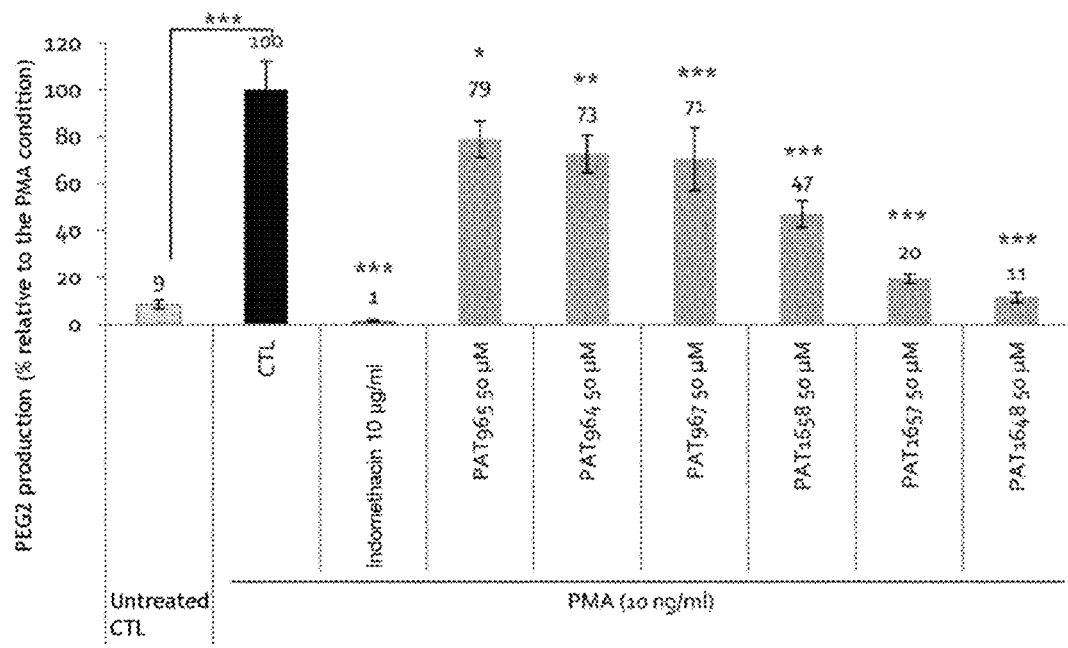
FIG. 5: Quantification of PGE2 production by NHEKs in the inflammatory state treated with compounds PAT965, PAT964, PAT967, PAT1658, PAT1657 or PAT1648. The results are expressed as a percentage of the condition treated with PMA (CTL) set at 100%. The graph shows the mean of the PGE2 measurements in supernatants from 3 independent cultures, as well as the standard deviation. The values $0.01<p<0.05$ are considered significant (*); $0.001<p<0.01$ highly significant () and $p<0.001$ very highly significant (*) (analysis of variance (ANOVA) and Dunnett comparison test against the PMA induced condition). Indomethacin was used as reference molecule.

The effect of the compounds on PGE2 production is presented in FIG. 5 and is expressed as a percentage of the PMA treatment set at 100%.

PGE2 production is indeed induced following PMA treatment and indomethacin reduces this PGE2 production in the culture supernatants to an almost undetectable level.

As for the compounds, they all reduce PGE2 production. Compounds PAT1648, PAT1657 and, to a lesser extent, compounds PAT1658 and PAT967 very highly significantly decrease the PGE2 level present in the culture supernatants.

Quantification of IL-6

Figure 6:
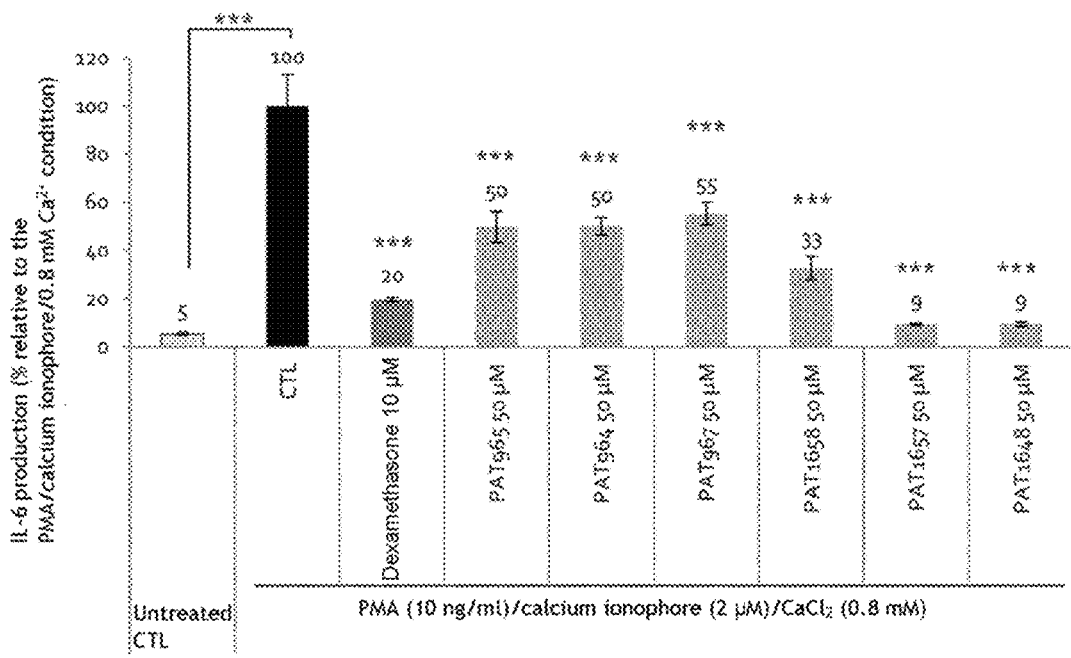
FIG. 6. Quantification of IL-6 production by NHEKs in the inflammatory state treated with compounds PAT965, PAT964, PAT967, PAT1658, PAT1657 or PAT1648. The results are expressed as a percentage of the condition treated with PMA combined with calcium ionophore in the presence of 0.8 mM Ca2+(CTL) set at 100%. The graph shows the mean of the IL-6 measurements in supernatants from 3 independent cultures, as well as the standard deviation. The values $p<0.001$ are considered very highly significant (***) (analysis of variance (ANOVA) and Dunnett comparison test against the condition induced with PMA/calcium ionophore/0.8 mM Ca2+). Dexamethasone was used as reference molecule.

The effect of the compounds on IL-6 production by NHEKs in the inflammatory state is shown in FIG. 6 and is expressed as a percentage of the treatment with PMA combined with calcium ionophore A23187 (under high-calcium conditions: 0.8 mM Ca2+).

Treatment with PMA combined with calcium ionophore in the presence of 0.8 mM Ca2+ indeed induces IL-6 overproduction. The reference molecule, namely dexamethasone, inhibits this IL-6 production in a very highly significant manner, which validates the test.

Once again, each of the compounds reduces, in a very highly significant manner, IL-6 production by NHEKs in an inflammatory state. The two compounds PAT1648 and PAT1657 allow the largest decreases and are more effective than dexamethasone itself.

Quantification of TNF-α

Figure 7:
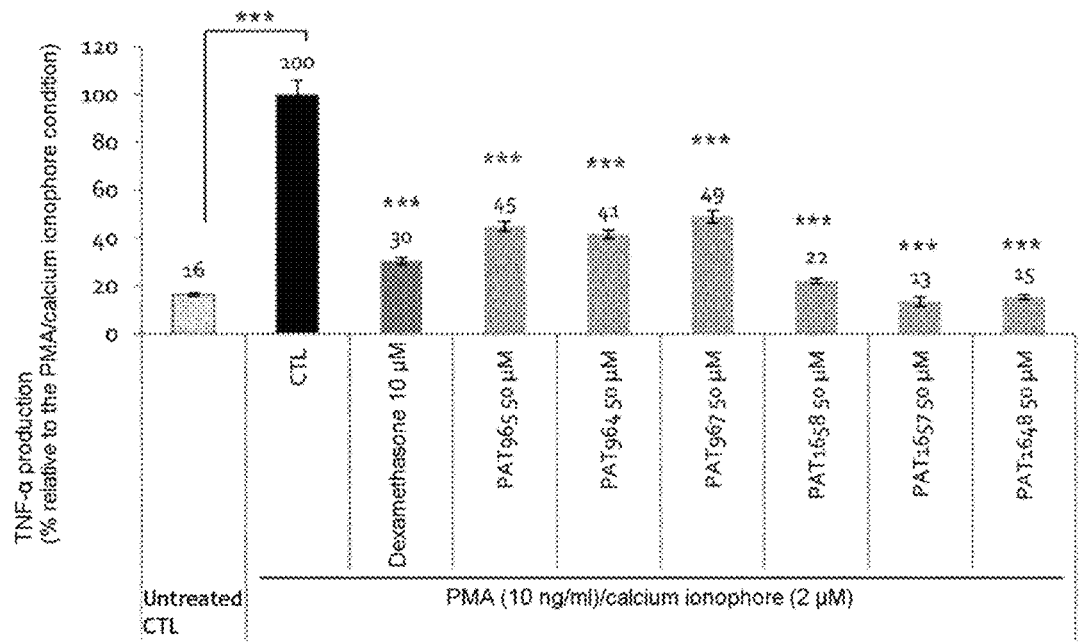
FIG. 7. Quantification of TNF-α production by NHEKs in the inflammatory state treated with compounds PAT965, PAT964, PAT967, PAT1658, PAT1657 or PAT1648. The results are expressed as a percentage of the condition treated with PMA combined with calcium ionophore in medium containing 0.06 mM Ca2+(CTL) set at 100%. The graph shows the mean of the TNF-α measurements in supernatants from 3 independent cultures, as well as the standard deviation. The values $p<0.001$ are considered very highly significant (***) (analysis of variance (ANOVA) and Dunnett comparison test against the condition induced with PMA/calcium ionophore). Dexamethasone was used as reference molecule.

The effect of the compounds on TNF-α production is shown in FIG. 7 relative to treatment with PMA combined with calcium ionophore A23187.

Treatment with PMA combined with calcium ionophore induces TNF-α secretion in keratinocyte culture supernatants. Dexamethasone at 10 µM has a very highly significant inhibitory effect on TNF-α production.

All of the compounds act as inhibitors of TNF-α production, and in a very highly significant manner. Again, compounds PAT1648 and PAT1657 have the most marked effects and are more effective than dexamethasone itself.

Quantification of $LTB_4$

Figure 8:
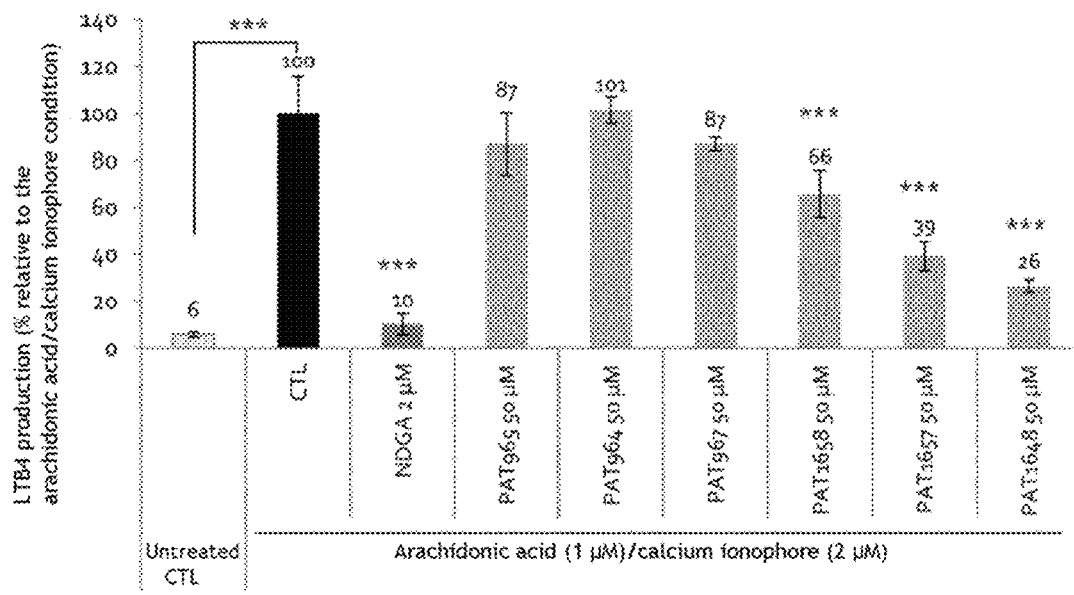
FIG. 8. Quantification of LTB4 production by NHEKs in the inflammatory state treated with compounds PAT965, PAT964, PAT967, PAT1658, PAT1657 or PAT1648. The results are expressed as a percentage of the condition treated with arachidonic acid combined with calcium ionophore (CTL) set at 100%. The graph shows the mean of the LTB4 measurements in supernatants from 3 independent cultures, as well as the standard deviation. The values $p<0.001$ are considered very highly significant (***) (analysis of variance (ANOVA) and Dunnett comparison test against the condition induced by arachidonic acid/calcium ionophore). Nordihydroguaiaretic acid (NDGA) was used as reference molecule.

The effects of the compounds on LTB4 production are shown in FIG. 8 and are expressed as a percentage of the treatment with arachidonic acid (a.a.) combined with calcium ionophore A23187 set at 100%.

Treatment of the cells with arachidonic acid combined with calcium ionophore induces LTB4 secretion. The reference molecule, namely NDGA, very highly significantly inhibits this LTB4 production in the kinetics studied.

Compounds PAT1648, PAT1657 and, to a lesser extent, compound PAT1658 also block/decrease, in a very highly significant manner, the LTB4 Level.

Evaluation of Cell Survival

NHEKs were brought into contact or not with the compounds to be tested. After 2 h, the cells underwent or not an inflammation treatment (10 ng/mL PMA/$H_2O$+2 µM calcium ionophore A23187/DMSO).

The cells were observed under an optical microscope 48 h after the inflammatory treatment.

Microscopic observation of the cultures after 48 h of incubation is presented in Table 6 below:

TABLE 6

Results of microscopic observation of the NHEK cultures 48 h after the inflammatory treatment.

| Group | Inflammation treatment received | Result at 48 h |
|---|---|---|
| Healthy control culture | No | Confluent culture: 100% cell survival |
| Pathological control culture | Yes | 10% cell survival |
| Culture + dexamethasone (reference molecule) | Yes | 10% cell survival |
| Culture + PAT965 | Yes | 10% cell survival |
| Culture + PAT964 | Yes | 10% cell survival |
| Culture + PAT967 | Yes | 10% cell survival |
| Culture + PAT1658 | Yes | 80% cell survival |
| Culture + PAT1657 | Yes | Confluent culture: 100% cell survival |
| Culture + PAT1648 | Yes | Confluent culture: 100% cell survival |

It is observed that the reference molecule (dexamethasone), as well as compounds PAT965, PAT964 and PAT967, have little or no effect on cell survival. Conversely, compounds PAT1658, and especially PAT1657 and PAT1648, show a strong cellular protection against inflammation.

However, it is remarkable that in the presence of compounds PAT1658, and especially PAT1657 and PAT1648, the keratinocytes are protected against inflammation-induced toxicity.

Conclusion

In general, the 6 compounds tested have remarkable anti-inflammatory effects.

According to the markers analysed, several of them (PAT1648 and PAT1657) have a protective effect superior to the internal controls considered as absolute references in this field (dexamethasone and indomethacin).

Furthermore, the 3 compounds PAT1648, PAT1657 and PAT1658 show a major protective effect on cytotoxicity induced in keratinocytes in the inflammatory state for 48H. These observations are based on microscopic analysis of the cells 48 h after the inflammatory treatment.

These 3 compounds thus have a remarkable cytoprotective and anti-inflammatory potential.

Example 3: Study of the Anti-Inflammatory Effect of Compound PAT1657 in Female SKH-1 Hairless Mice Subjected to Induction of Skin Inflammation by Repeated Cutaneous Applications of Acetone Solution of TPA (12-O-tetradecanoylphorbol-13-acetate)

Materials and Methods

Animals

The study is performed on 18 female SKH-1 hairless mice, weighing roughly 20-25 g and divided into 3 groups (n=6/housed in pairs) under controlled temperature (24±2° C.) and humidity (50±20%) conditions and with a 12-hour reversed light cycle (light from 21:00 to 09:00) (food and water ad libitum).

Compounds to be Tested

The compounds to be tested are as follows:

Excipial® ointment (control)

PAT1657 (octyl-isochlorogenamide A) incorporated at 1.33% or 2.67% by mass in Excipial® ointment The treatment groups are distributed as follows:
G1: induced skin inflammation+daily treatment with vehicle (Excipial® ointment) (Control),
G2: induced skin inflammation+treatment with PAT1657 incorporated at 1.33% by mass in Excipial® ointment (PAT1657/1.33%),
G3: induced skin inflammation+treatment with PAT1657 incorporated at 2.67% by mass in Excipial® ointment (PAT1657/2.67%).

Induction and Maintenance of Skin Inflammation

Skin inflammation is induced for each mouse by daily dorsal cutaneous application to Zone A (FIG. 9) for 7 days (day 1 to day 7) of 100 µL of TPA acetone solution at a concentration of 0.2 mg/ml.

It is then maintained by cutaneous application every 2 days for 7 days (day 8 to day 14) of 100 µl of TPA acetone solution.

The TPA acetone solution is placed in contact with the same skin zone for each mouse using a restraint system.

Animal Treatments

Treatments began 7 days after the initiation of induction of skin inflammation (day 8).

Figure 9:
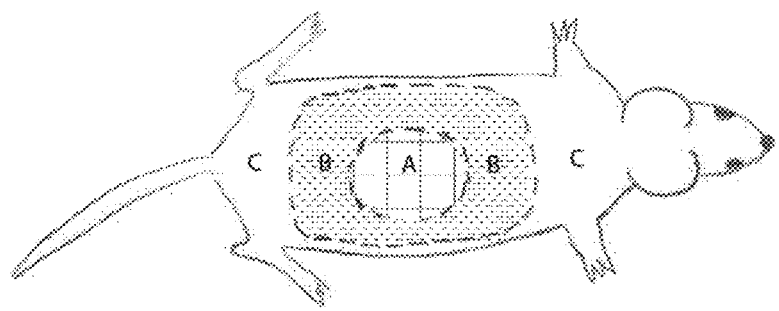
FIG. 9. Dorsal-view diagram of a mouse showing the various application zones. Zone A: TPA acetone solution application zone; Zones A and B: ointment application zones (control and two concentrations of compound PAT1657); Zone C: the rest of the back not receiving an application.

For the vehicle, the animals (G1) were treated daily by cutaneous application of 0.125 g of ointment on the backs of the mice just off the zone of application of TPA acetone solution (roughly 5 cm$^2$ area corresponding to zones A and B shown in FIG. 9), for 7 days from day 8 to day 14.

For compound PAT1657, the animals (G2 and G3) were treated by cutaneous application of 0.125 g of ointment on the backs of the mice just off the zone of application of TPA acetone solution (roughly 5 cm$^2$ area corresponding to zones A and B shown in FIG. 9), on days 8, 11 and 14.

On days when TPA acetone solution was applied, the ointments were applied about 1 hour after application of TPA acetone solution.

Animal Monitoring

The animals were observed daily before and after treatment,

The animals were weighed once a week.

Macroscopic Visual Scoring of Skin Inflammation

Macroscopic visual scoring of skin inflammation is performed daily for each mouse from day 8 to day 15 by quantifying it according to the following scale (Guenon-Macé et al., 2015):

0: no or no further inflammation
1: mild
2: moderate
3: severe
4: very severe

Macroscopic visual scoring of skin inflammation makes it possible to quantify the following parameters:
degree of skin inflammation in the TPA acetone solution application zone and in the ointment treatment zone corresponding to zone A in FIG. 9,
degree of skin inflammation in the ointment treatment zone and outside the TPA acetone solution application zone corresponding to zone B in FIG. 9,
degree of skin inflammation on the rest of the back corresponding to zone C in FIG. 9,
Overall macroscopic score of skin inflammation (total of the scores of the three zones A, B and C shown in FIG. 9).

Result

Animal Mortality

No mortality was observed in any treatment group during the experiment.

Animal Behaviour

No abnormal behaviour was observed in any treatment group during the experiment. No significant differences in weight in any treatment group were observed during the experiment.

Reaction to Application of the Products to be Tested

No reaction was observed in any group treated with the ointments tested (control and PAT1657) during the experiment.

Macroscopic Scoring of Skin Inflammation

Figure 10:
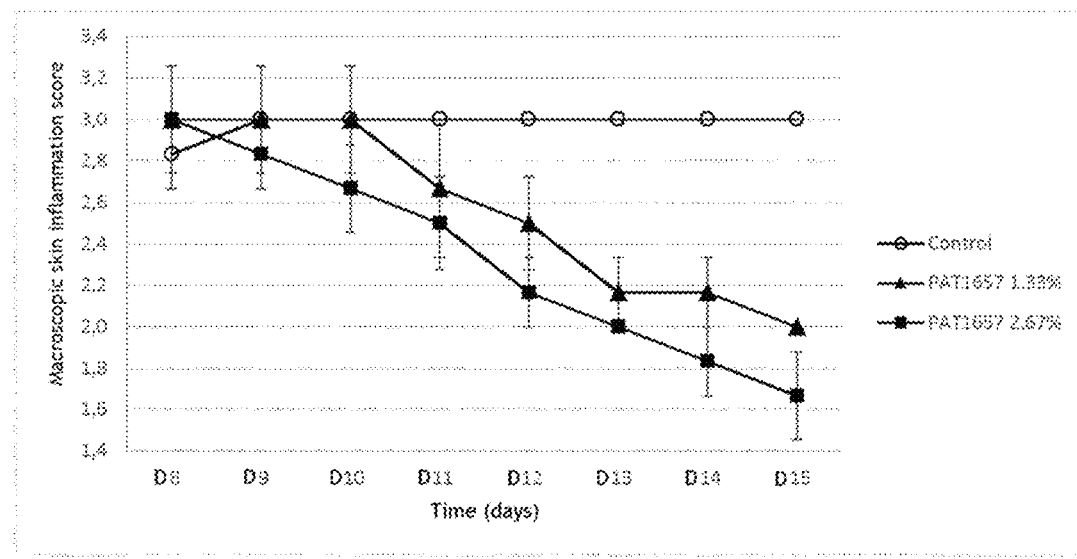
FIG. 10. Curve representing the degree of inflammation in the TPA acetone solution application zone and in the treatment zone (zone A, FIG. 9). The curves represented by circles, triangles and squares correspond respectively to the control (Excipial® ointment alone) and to treatment with compound PAT1657 incorporated at 1.33% and 2.67% in Excipial® ointment.

The results of the measurements of degree of skin inflammation at the TPA acetone solution application zone and the treatment zone (zone A, FIG. 9) as a function of the treatment used (control and two concentrations of PAT1657) are shown in FIG. 10. A significant decrease in macroscopic visual scoring of skin inflammation was observed for compound PAT1657 at the two doses tested relative to the control from day 13 onwards.

Figure 11:
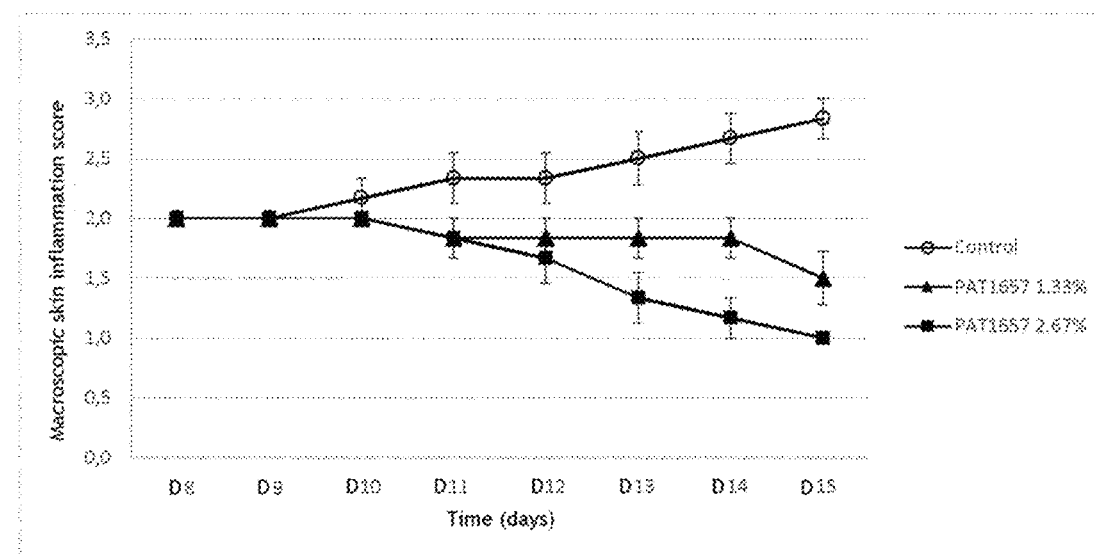
FIG. 11. Curve representing the degree of inflammation in the treatment application zone and outside the TPA acetone solution application zone (zone B, FIG. 9). The curves represented by circles, triangles and squares correspond respectively to the control (Excipial® ointment alone) and to treatment with compound PAT1657 incorporated at 1.33% and 2.67% in Excipial® ointment.

The results of measurements of degree of skin inflammation at the treatment zone and outside the TPA acetone solution application zone (zone B, FIG. 9) as a function of the treatment used (control and two concentrations of PAT1657) are shown in FIG. 11. A significant decrease in macroscopic visual scoring of skin inflammation was observed for compound PAT1657 at the two doses tested relative to the control from day 13 onwards.

Figure 12:
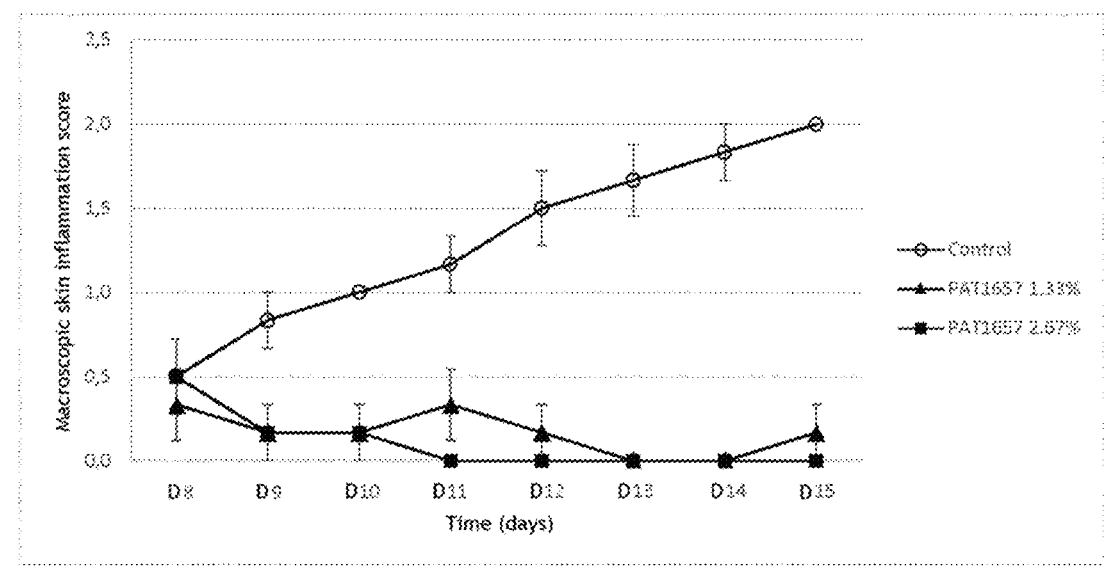
FIG. 12. Curve representing the degree of inflammation in the rest of the back (zone C, FIG. 9). The curves represented by circles, triangles and squares correspond respectively to the control (Excipial® ointment alone) and to treatment with compound PAT1657 incorporated at 1.33% and 2.67% in Excipial® ointment.

The results of measurements of degree of skin inflammation in the rest of the back (zone C, FIG. 9) as a function of the treatment used (control and two concentrations of PAT1657) are shown in FIG. 12. There was a significant decrease in the degree of inflammation for compound PAT1657 at the two doses tested relative to the control from day 10 onwards.

Figure 13:
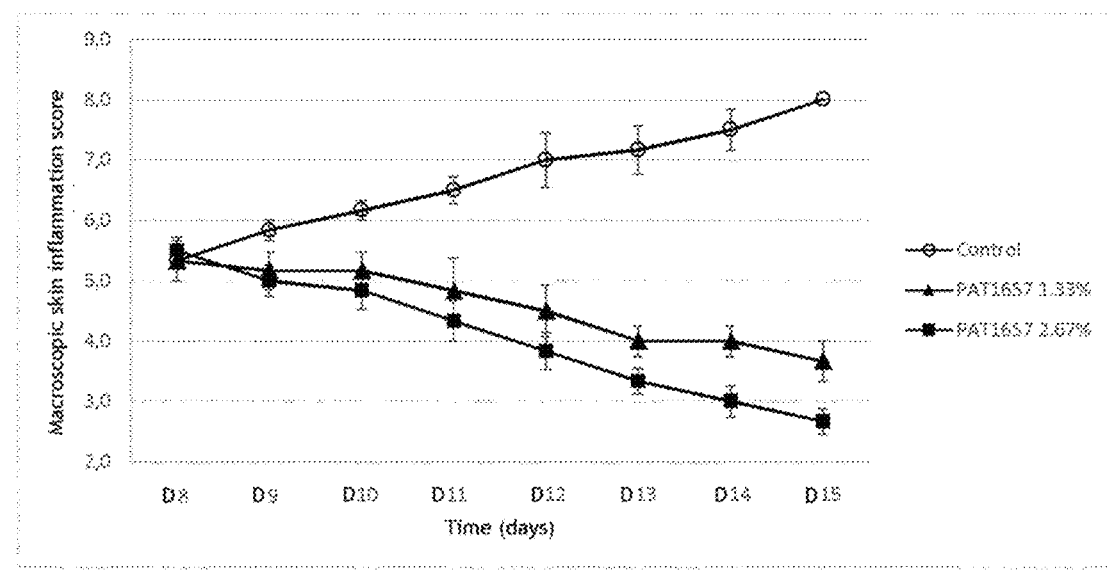
FIG. 13. Curve representing the overall macroscopic skin inflammation score (sum of zones A, B and C) as a function of treatment. The curves represented by circles, triangles and squares correspond respectively to the control (Excipial® ointment alone) and to treatment with compound PAT1657 incorporated at 1.33% and 2.67% in Excipial® ointment.

The results of measurements of overall degree of skin inflammation (zones A, B and C, FIG. 9) as a function of the treatment used (control and two concentrations of PAT1657) are shown in FIG. 13. A significant decrease in macroscopic visual scoring of skin inflammation was observed for compound PAT1657 at the two doses tested relative to the control from day 10 onwards.

Conclusion

Compound PAT1657 at the two doses tested, administered by cutaneous application every 3 days, as a curative treatment in female SKH-1 hairless mice subjected to induction of skin inflammation, significantly reduced the intensity of the latter from a macroscopic point of view with a dose-dependent effect.

Example 4: Study of the Effect of Compound PAT1657 on the Treatment of Imiquimod-Induced Psoriasis in Balb/c Mice Materials and Methods Animals The study is performed on 40 female Balb/c mice, weighing roughly 18-20 g and randomized by weight into 5 groups (n=8) as function of the treatments, under controlled temperature (24±2° C.) and humidity (50±20%) conditions and with a 12-hour reversed light cycle (light from 20:00 to 08:00) (food and water ad libitum).

Compounds to be Tested

The compounds to be tested are as follows:
Excipial® neutral ointment (control)
PAT1657 (octyl-isochlorogenamide A) incorporated at 1.33% or 2.67% by mass in Excipial® ointment Aldara® cream containing 5% imiquimod, an inducer of psoriasis Dermoval® cream containing 0.05% clobetasol propionate and used for topical treatment of psoriasis (reference product)

The treatment groups are distributed as follows:

Group 1: no induction of psoriasis but cutaneous application of neutral ointment from day 1 to day 10 and treatment with Excipial® neutral ointment from day 7 to day 10 (negative control) (EP/EP);

Group 2: induction of psoriasis by cutaneous application of Aldara® cream containing imiquimod from day 1 to day 10 and treatment with Excipial® neutral ointment from day 7 to day 10 (positive control) (ALD/EP);

Group 3: induction of psoriasis by cutaneous application of Aldara® cream containing imiquimod from day 1 to day 10 and treatment with neutral ointment containing 1.33% compound PAT1657 from day 7 to day 10 (ALD/PAT1657-1.33%);

Group 4: induction of psoriasis by cutaneous application of Aldara® cream containing imiquimod from day 1 to day 10 and treatment with neutral ointment containing 2.67% compound PAT1657 from day 7 to day 10 (ALD/PAT1657-2.67%);

Group 5: induction of psoriasis by cutaneous application of Aldara® cream containing imiquimod from day 1 to day 10 and treatment with Dermoval® cream from day 7 to day 10 (ALD/Dermoval®).

Induction and Maintenance of Psoriasis

To perform the induction of psoriasis, it was necessary to remove the hair from the backs of the animals by shaving and plucking to have direct access to the skin tissue. Psoriasis was induced in all mice in groups 2 to 5 by daily cutaneous application for 10 days, from day 1 to day 10, of roughly 70 mg of Aldara® cream. The cream was applied to the shaved backs of the mice with a silk brush. For the mice in group 1, daily cutaneous application of Excipial® neutral ointment was carried out under the same conditions: roughly 70 mg was applied for 10 days, from day 1 to day 10, in the morning using a silk brush.

Animal Treatments

The ointments containing compound PAT1657 at the two doses to be tested, Excipial® neutral ointment and Dermoval® cream, were administered by cutaneous applications for 4 days, from day 7 to day 10, on the backs of the mice in the psoriasis induction region. For each application, roughly 100 mg of ointment or cream was applied with a silk brush, at least 4 hours after application of Aldara® cream or Excipial® neutral ointment for induction or not of psoriasis.

Psoriasis Area and Severity Index (PASI)

The psoriasis area and severity index (PASI) was calculated daily throughout the experiment from day 1 to day 11, based on the following three parameters:

Presence of erythema, i.e. skin redness, in the psoriasis induction region, scored as follows: 0=no or no further erythema; 1=mild erythema; 2=moderate erythema; 3=severe erythema; 4=very severe erythema.

Degree of induration, i.e. skin hardening and thickening, in the psoriasis induction region, scored as follows: 0=no or no further induration; 1=mild induration; 2=moderate induration; 3=severe induration; 4=very severe induration.

Degree of desquamation, i.e. presence of plaques on the skin surface, in the psoriasis induction region, scored as follows: 0=no or no further desquamation; 1=mild desquamation; 2=moderate desquamation; 3=severe desquamation; 4=very severe desquamation.

The psoriasis area and severity index is the sum of the scores for these three parameters.

Statistical Analyses

The scores for presence of erythema, degree of induration and desquamation, and the psoriasis area and severity index (PASI) were analysed at the end of the experiment. A non-parametric analysis of variance (ANOVA) was performed using the Kruskal-Wallis test followed, in the event of significance, by the Mann-Whitney test to compare the treated groups with the EP/EP negative control, ALD/EP positive control and ALD/Dermoval® groups. Statistical processing was performed using the Statview®5 software (SAS, Institute Inc., USA) and the differences were considered significant for values of $p<0.05$.

Result

Animal Mortality

No mortality was observed during the experiment in the four treatment groups.

Animal Behaviour

No abnormal animal behaviour was observed during the experiment in the four treatment groups.

Psoriasis Area and Severity Index (PASI)

Presence of Erythema in the Psoriasis Induction Region

During the period of psoriasis maintenance and treatment application between day 8 and day 11, the following significant differences were observed:

For day 8, the mean scores for presence of erythema in the psoriasis induction region of mice in the ALD/PAT1657-1.33%, ALD/PAT1657-2.67% and ALD/Dermoval® groups were significantly lower than that of mice in the ALD/EP group ($p=0.001$; $p=0.007$ and $p=0.007$, respectively).

For day 9, the mean scores for presence of erythema in the psoriasis induction region of mice in the ALD/PAT1657-1.33%, ALD/PAT1657-2.67% and ALD/Dermoval® groups were significantly lower than that of mice in the ALD/EP group ($p=0.002$; $p=0.002$ and $p=0.004$, respectively).

For day 10, the mean scores for presence of erythema in the psoriasis induction region of mice in the ALD/PAT1657-1.33%, ALD/PAT1657-2.67% and ALD/Dermoval® groups were significantly lower than that of mice in the ALD/EP group ($p=0.001$ in all cases). The mean score for presence of erythema in the psoriasis induction region of mice in the ALD/PAT1657-1.33% group was significantly lower than that of mice in the ALD/Dermoval® group ($p=0.037$), and that of mice in the ALD/PAT1657-2.67% group showed a tendency to be significantly lower than that of mice in the ALD/Dermoval® group ($p=0.079$).

For day 11, the mean scores for presence of erythema in the psoriasis induction region of mice in the ALD/PAT1657-1.33%, ALD/PAT1657-2.67% and ALD/Dermoval® groups were significantly lower than that of mice in the ALD/EP group ($p=0.001$ in all cases). The mean scores for presence of erythema in the psoriasis induction region of mice in the ALD/PAT1657-1.33% and ALD/PAT1657-2.67% groups were significantly lower than those of mice in the ALD/Dermoval® group ($p=0.001$ and $p=0.014$, respectively).

Degree of Induration in the Psoriasis Induction Region

During the period of psoriasis maintenance and treatment application between day 8 and day 11, the following significant differences were observed:

For day 8, the mean scores for degree of induration in the psoriasis induction region of mice in the ALD/PAT1657-1.33%, ALD/PAT1657-2.67% and ALD/Dermoval® groups were significantly lower than that of mice in the ALD/EP group (p=0.001; p=0.004 and p=0.001, respectively).

For day 9, the mean scores for degree of induration in the psoriasis induction region of mice in the ALD/PAT1657-1.33%, ALD/PAT1657-2.67% and ALD/Dermoval® groups were significantly lower than that of mice in the ALD/EP group (p=0.001; p=0.001 and p=0.001, respectively). The mean score for degree of induration in the psoriasis induction region of mice in the ALD/PAT1657-1.33% group was significantly higher than that of mice in the ALD/Dermoval® group (p=0.015).

For day 10, the mean scores for degree of induration in the psoriasis induction region of mice in the ALD/PAT1657-1.33%, ALD/PAT1657-2.67% and ALD/Dermoval® groups were significantly lower than that of mice in the ALD/EP group (p=0.001 in all cases). The mean scores for degree of induration in the psoriasis induction region of mice in the ALD/PAT1657-1.33% and ALD/PAT1657-2.67% groups were significantly higher than those of mice of the ALD/Dermoval® group (p=0.025) in both cases.

For day 11, the mean scores for degree of induration in the psoriasis induction region of mice in the ALD/PAT1657-1.33%, ALD/PAT1657-2.67% and ALD/Dermoval® groups were significantly lower than that of mice in the ALD/EP group (p=0.001 in all cases). The mean score for degree of induration in the psoriasis induction region of mice in the ALD/PAT1657-1.33% group showed a tendency to be significantly higher than that of mice in the ALD/Dermoval® group (p=0.063).

Degree of Desquamation in the Psoriasis Induction Region

During the period of psoriasis maintenance and treatment application between day 8 and day 11, the following significant differences were observed:

For day 8, the mean scores for degree of desquamation in the psoriasis induction region of mice in the ALD/PAT1657-1.33%, ALD/PAT1657-2.67% and ALD/Dermoval® groups were significantly lower than that of mice in the ALD/EP group (p=0.007; p=0.006 and p=0.013, respectively).

For day 9 and day 10, the mean scores for degree of desquamation in the psoriasis induction region of mice in the ALD/PAT1657-1.33%, ALD/PAT1657-2.67% and ALD/Dermoval® groups were significantly lower than that of mice in the ALD/EP group (p=0.001 in all cases).

For day 11, the mean scores for degree of desquamation in the psoriasis induction region of mice in the ALD/PAT1657-1.33%, ALD/PAT1657-2.67% and ALD/Dermoval® groups were significantly lower than that of mice in the ALD/EP group (p=0.001 in all cases). The mean score for degree of desquamation in the psoriasis induction region of mice in the ALD/PAT1657-1.33% group was significantly higher than that of mice in the ALD/Dermoval® group, and that of mice in the ALD/PAT1657-2.67% group tended to be significantly higher than that of mice in the ALD/Dermoval® group (p=0.059).

Psoriasis area and severity index (PASI)

Figure 14:
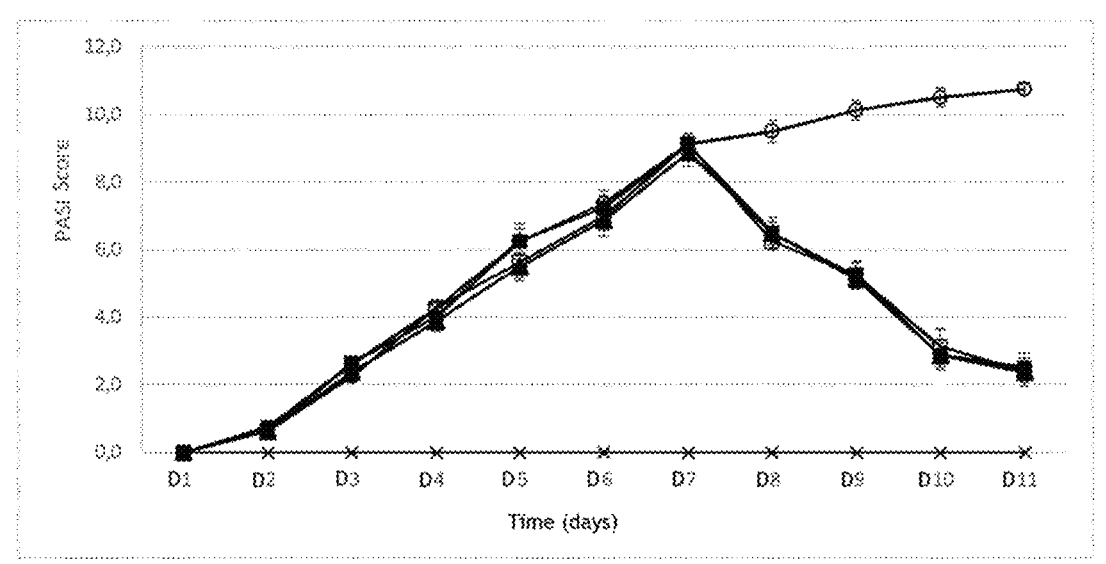
FIG. 14. Curve representing the mean psoriasis area and severity index (PASI, on the y-axis) of mice in the 5 treatment groups during the experiment (time in days on the x-axis). The curves represented by circles, crosses, black triangles, white squares and black squares correspond respectively to the ALD/EP positive control (induction of psoriasis and application of Excipial® neutral ointment), to the EP/EP negative control (no induction of psoriasis and application of Excipial® neutral ointment), to treatment with the reference compound Dermoval® (ALD/Dermoval®), and to treatment with compound PAT1657 incorporated at 1.33% (ALD/PAT/PAT 1657-1.33%) and 2.67% (ALD/PAT 1657-2.67%) in Excipial® ointment.

The psoriasis area and severity index (PASI) is the sum of the scores for presence of erythema, degree of induration and degree of desquamation in the psoriasis induction and treatment regions. FIG. 14 shows the mean psoriasis area and severity indexes for mice in the 5 treatment groups during the experiment.

The Kruskal-Wallis test shows that there was no significant difference between the mean psoriasis area and severity indexes for mice in the 5 treatment groups before the initiation of induction of psoriasis on day 1.

During the psoriasis induction period and before the initiation of treatment between day 2 and day 7, the mean psoriasis area and severity indexes of mice in the ALD/EP, ALD/PAT1657-1.33%, ALD/PAT1657-2.67% and ALD/Dermoval® groups were significantly higher than those of mice in the EP/EP group shown in FIG. 14 by the curve with crosses merging with the x-axis (p=0.009; p=0.009; p=0.003 and p=0.009, respectively for day 2, and p=0.001 in all cases for day 3 to day 7).

During the period of psoriasis maintenance and treatment application between day 8 and day 11, the following significant differences were observed:

For day 8, the mean psoriasis area and severity indexes for mice in the ALD/PAT1657-1.33%, ALD/PAT1657-2.67% and ALD/Dermoval® groups were significantly lower than that of mice in the ALD/EP group represented in FIG. 14 by the curve with circles (p=0.001; p=0.001 and p=0.001, respectively).

For day 9, day 10 and day 11, the mean psoriasis area and severity indexes for mice in the ALD/PAT1657-1.33%, ALD/PAT1657-2.67% and ALD/Dermoval® groups were significantly lower than that of mice in the ALD/EP group represented in FIG. 14 by the curve with circles (p=0.001 in all cases).

Conclusion

Compound PAT1657 at the two doses tested showed significant effects on the treatment of psoriasis. Compound PAT1657 significantly decreased, and in a manner comparable to Dermoval® cream, the presence of erythema in the psoriasis induction region, the degree of induration in the psoriasis induction region and the degree of desquamation in the psoriasis induction region, thus significantly decreasing the psoriasis area and severity index.

Example 5: Characterization of Compound PAT1657 in Terms of a Skin Benefit

The study consisted in measuring the effects of compound PAT1657 by qRT-PCR on the expression of 94 genes involved in dermal biology, connective tissue remodelling and ageing.

The protocol consisted in applying compound PAT1657 for 24 h in the culture medium of Normal Human Dermal Fibroblasts (NHDFs) in monolayer and analysing the various RNA populations to identify the genes differentially expressed by real-time qRT-PCR.

Materials and Methods

The study was carried out on Normal Human Dermal Fibroblasts (NHDFs) (ATCC, CRL-2522, origin: foreskin) at about 40% of their proliferative potential and grown in monolayer in DMEM medium (Invitrogen, 31885-049) containing antibiotics (penicillin/streptomycin, Invitrogen, 15140-122) but not containing serum. The cells were maintained in a humid atmosphere at 37° C. containing 5% $CO_2$.

A preliminary cytotoxicity study defined a working concentration of 4 µM (prepared in DMSO) for compound PAT1657 for the gene expression study.

Compound PAT1657 was applied in the NHDF culture medium for 24 h (n=3). Controls treated with the solvent DMSO (1% for the NHDFs) in which the active agents were prepared were also analysed. At the end of the treatments, total RNA populations were extracted, their integrity was analysed by capillary electrophoresis, and gene expression differences were analysed by qRT-PCR using 96-well TaqMan microfluidic cards (custom produced by Applied Biosystems), targeting key functions of the dermis and epidermis. The technical details of the implementation of the present paragraph are explained in the "Materials and methods" section of Example 1 of patent application FR1650745 and more specifically the sub-section titled "Analysis of gene expression changes" (page 26 line 22 to page 28 line 9).

The gene expression changes induced by the active agents are expressed as relative quantity (RQ) based on the respective DMSO solvent controls.

Results

Compound PAT1657 induces many remarkable inductions.

The results are summarized in the form of a table (Table 7) indicating genes representative of a beneficial cosmetic effect, varying significantly, with compound PAT1657 applied for 24 h to Normal Human Dermal Fibroblasts (NHDFs).

TABLE 7

Genes that increase significantly with extract PAT1657 (at 4 µM) applied for 24 h to Normal Human Dermal Fibroblasts (NHDFs). Gene symbols, gene names, relative expression (RQ) based on the 1% DMSO vehicle and p-values are shown.

| Gene symbol | Gene name | RQ | p-value |
| --- | --- | --- | --- |
| CCL5 | Chemokine (C-C motif) ligand 5 | 28.13 | 0.0006 |
| VEGFA | Vascular endothelial growth factor A | 8.28 | 0.0001 |
| MMP1 | Matrix metalloproteinase 1 (interstitial collagenase) | 6.91 | 0.0447 |
| POU5F1 | POU domain, class 5, transcription factor 1 (POU5F1) | 5.10 | 0.0305 |
| NANOG | Homeobox protein NANOG | 4.67 | 0.0406 |
| SOD2 | Superoxide dismutase 2, mitochondrial | 4.66 | 0.001 |
| RORA | Retinoid-related orphan receptor-alpha | 4.41 | 0.0317 |
| GADD45A | Growth arrest and DNA-damage-inducible, alpha | 3.68 | 0.0024 |
| MMP3 | Matrix metalloproteinase 3 (stromelysin 1) | 3.12 | 0.007 |
| TXNRD1 | Thioredoxin reductase 1 | 2.82 | 0.0007 |
| DDIT3 | DNA-damage-inducible transcript 3 protein | 2.81 | 0.0056 |
| FTL | Ferritin, Light polypeptide 1 | 2.08 | 0.0005 |
| SIRT1 | NAD-dependent deacetylase sirtuin-1 | 2.02 | 0.0047 |
| KLF4 | Krüppel-like factor 4 | 1.93 | 0.0147 |
| MTNR1A | Melatonin receptor type 1A | 1.46 | 0.0014 |
| NOX1 | NADPH oxidase 1 | 1.46 | 0.0014 |
| RBP2 | Retinol-binding protein 2 | 1.46 | 0.0014 |

Healing Effect:

Accelerated healing is notably facilitated by migration of fibroblasts to the skin lesion site, stimulation of angiogenesis, and deposition of collagen. Compound PAT1657 increases the expression of the CCL5 (28.13×) and VEGFA (8.3×) genes encoding respectively a chemokine and an angiogenesis mediator which play a role in skin healing. It has been shown that this chemokine plays an important role in the skin healing process. It is involved in the migration of dermal stem cells (DSC) to the skin lesion site. This process is essential for re-epithelialization, repopulation of fibroblasts in the dermis, and angiogenesis (Kroeze et al., 2009).

Several genes encoding proteins involved in extracellular matrix remodelling are induced, such as MMP1 (6.9×) and MMP3 (3.1×). Metalloproteinases (MMPs) play a role in the skin wound repair process through extracellular matrix remodelling (Stevens et al., 2012). Metalloproteinase 1 (MMP1) initiates the cleavage of type I and III collagen fibrils in the skin. This process of collagen degradation is then continued by MMP3 (Krieg et al., 2011).

Compound PAT1657 could therefore prove to promote healing by accelerating the re-epithelialization of keratinocytes and angiogenesis and by thus promoting wound closure.

Regenerating Effect:

The POU5F1 and NANOG and KLF4 genes are dermal stem cell markers (5.1×, 4.7× and 1.9×, respectively). They participate in the process of reprogramming differentiated cells into pluripotent stem cells. The latter are important for maintaining dermal homeostasis, repairing damage, and regenerating tissues (Jerabek et al., 2014).

Anti-Ageing Effect:

Many genes involved in the oxidative stress response are also overexpressed: SOD2 (4.7×), RORA (4.4×), TXNRD1 (2.8×), FTL (2.1×), MTNR1A, NOX1, RBP2 and GSS. Superoxide dismutase 2 encoded by the SOD2 gene is a mitochondrial protein involved in the first line of defence against ROS. It converts the superoxide anion into hydroperoxide, which in turn is converted into oxygen and water by catalase and peroxiredoxins (Weyemi et al., 2012).

Genes encoding proteins involved in mechanisms for repairing DNA damaged by cell stress also increase their expression: DDIT3, GADD45A and SIRT1.

The overexpression of several of these genes shows the ability of compound PAT1657 to reduce the effects of pro-oxidant stress generating an excess of free radicals, such as UV rays accelerating the signs of skin ageing, or to combat various pro-inflammatory skin pathologies or conditions which also generate reactive oxygen species.

REFERENCES

Barañano et al.: PNAS, Vol. 58, NO. 25, PP. 16093-16098, December 2002.

Fitzpatrick, et al.: Journal of Pharmacology and Experimental Therapeutics, Vol. 299, NO. 3, PP. 915-920, December 2001.

Gianfranco Peluso et al.; Journal of Natural Products, Vol. 58, NO. 5, pp. 639-646, May 1995 (Abstract).

Jerabek et al.: Biochimica et Biophysica Acta (BBA)—Gene Regulatory Mechanisms, Vol. 1839, Issue 3, PP. 138-154, March 2014.

Krieg et al.: Experimental Dermatology, Vol. 20, NO. 8, PP. 689-695, August 2011.

Lee, S A et al.: Pharmacology, Vol. 90, Issue 3-4, PP. 183-192, August 2012.

Kroeze et al.: Journal of Investigative Dermatology, Vol. 129, NO. 6, PP. 1569-1581, June 2009.

Otterbein et al.: American Journal of Pathology, Vol. 163, NO. 6, PP. 2555-2563, December 2003.

Stevens et al.: Molecular Biology of the Cell, Vol. 23, NO. 6, PP. 1068-1079, March 2012.

Stocker et al.: PNAS, Vol. 84, PP. 5918-5922, August 1987.

Xinyu Wang et al.: European Journal of Pharmacology, Vol. 635, PP. 16-22, March 2010.

Guenin-Macé et al.: Science Translational Medicine, Vol. 7, Issue 289, PP. 289ra85, May 2015.

Weyemi et al.: Aging, Vol. 4, NO. 2, PP. 116-118, February 2012.

The invention claimed is:

1. A compound or a mixture of compounds of general formula (IA)

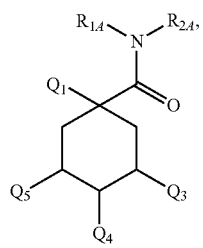

(IA)

wherein
R$_{1A}$ and R$_{2A}$ represent, independently of each other:
H, provided that R$_{1A}$ and R$_{2A}$ are not both a hydrogen atom,
a butyl group,
a C$_7$-C$_{30}$ alkyl group,
a butyl or C$_7$-C$_{24}$ alkyl group covalently linked to a C$_6$-C$_{18}$ aryl group or a C$_6$-C$_{18}$ aryl group covalently linked to butyl or a C$_7$-C$_{24}$ alkyl group, or
a C$_7$-C$_{18}$ aryl group;
and
Q$_1$, Q$_3$, Q$_4$ and Q$_5$ represent, independently of each other, an OH group, caffeoyl group, maloyl group, caffeoylmaloyl group or maloylcaffeoyl group, provided that at least one of these radicals is not an OH group,
or a pharmaceutically acceptable salt or stereoisomer or hydrate thereof,
with the proviso that compounds in which either Q$_3$ or Q$_5$ represents a caffeoyl group and Q$_1$, Q$_4$ and the other of Q$_3$ or Q$_5$ represent an OH group are excluded.

2. The compound of claim 1, wherein Q$_1$, Q$_3$, Q$_4$ and Q$_5$ represent, independently of each other, an OH group or caffeoyl group, provided that at least one of these radicals is not an OH group, with the proviso that compounds in which either Q$_3$ or Q$_5$ represents a caffeoyl group and Q$_1$, Q$_4$ and the other of Q$_3$ or Q$_5$ represent an OH group are excluded.

3. The compound of claim 1, wherein Q$_1$ represents an OH group.

4. The compound of claim 1, wherein R$_{1A}$ is a hydrogen atom.

5. The compound of claim 1, wherein Q$_1$ and Q$_4$ represent an OH group, Q$_3$ and Q$_5$ represent a caffeoyl group, R$_{1A}$ is a hydrogen atom and R$_{2A}$ is a butyl, octyl, dodecyl, octadecyl, phenylbutyl or naphthyl group.

6. A method for producing a compound of general formula (IA)

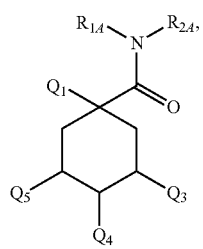

(IA)

wherein
R$_{1A}$ and R$_{2A}$ represent, independently of each other:
H, provided that R$_{1A}$ and R$_{2A}$ are not both a hydrogen atom,
a butyl group,
a C$_7$-C$_{30}$ alkyl group,
a butyl or C$_7$-C$_{24}$ alkyl group covalently linked to a C$_6$-C$_{18}$ aryl group or a C$_6$-C$_{18}$ aryl group covalently linked to butyl or a C$_7$-C$_{24}$ alkyl group, or
a C$_7$-C$_{18}$ aryl group;
and
Q$_1$, Q$_3$, Q$_4$ and Q$_5$ represent, independently of each other, an OH group, caffeoyl group, maloyl group, caffeoylmaloyl group or maloylcaffeoyl group, provided that at least one of these radicals is not an OH group,
or a pharmaceutically acceptable salt or stereoisomer or hydrate thereof, with the proviso that compounds in which either Q$_3$ or Q$_5$ represents a caffeoyl group and Q$_1$, Q$_4$ and the other of Q$_3$ or Q$_5$ represent an OH group are excluded,
wherein the method comprises a step a) during which a poly-substituted quinic acid of formula (IV)

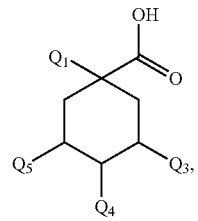

(IV)

wherein Q$_1$, Q$_3$, Q$_4$ and Q$_5$ are as defined as above, reacts with a compound of formula HNR$_{1A}$R$_{2A}$.

7. The method of claim 6, wherein Q$_1$, Q$_3$, Q$_4$ and Q$_5$ represent, independently of each other, an OH group or caffeoyl group, provided that at least one of these radicals is not an OH group, and with the proviso that compounds in which either Q$_3$ or Q$_5$ represents a caffeoyl group and Q$_1$, Q$_4$ and the other of Q$_3$ or Q$_5$ represent an OH group are excluded.

8. The method of claim 6, wherein the poly-substituted quinic acid of formula (IV) is 3,5-di-O-caffeoylquinic acid.

9. The method of claim 6, wherein R$_{1A}$ is a hydrogen atom.

10. The method of claim 6, wherein the compound of formula HNR$_{1A}$R$_{2A}$ is selected from one of the following compounds: octan-1-amine, butan-1-amine, laurylamine, 1-octadecylamine, 4-phenylbutan-1-amine, or 2-naphthylamine.

11. The method of claim 6, wherein step a) is preceded by a step of activating the carboxyl group of the poly-substituted quinic acid of formula (IV) with a carboxyl group activator.

12. A compound obtainable by the method of claim 9.

13. A method for treating inflammation or inflammatory disease, comprising administering to a patient in need thereof, a therapeutically effective amount of at least one compound according to claim 1.

14. A methold for treating inflammation or for promoting healing of dermal tissues, comprising administering to a patient in need thereof, a therapeutically effective amount of at least one pharmaceutical composition comprising at least one compound according to claim 1.

15. A cosmetic method for reducing the effect of pro-oxidanat stress on skin and/or for promoting the regeneration of dermal tissues, comprising administering to a patient in need thereof, an effective amount of at least one cosmetic composition comprising at least one compound according to claim 1.

16. The compound of claim 1, wherein any two of radicals $Q_1$, $Q_3$, $Q_4$ and $Q_5$ represent a caffeoyl group, and the other two represent an OH group, with the proviso that compounds in which either $Q_3$ or $Q_5$ represents a caffeoyl group and $Q_1$, $Q_4$ and the of other $Q_3$ or $Q_5$ represent an OH group are excluded.

17. The compound of claim 1, wherein $Q_1$ and $Q_4$ represent an OH group.

18. The compound of claim 1, wherein $R_{14}$ is a hydrogen atom and $R_{24}$ is a butyl group or a $C_7$-$C_{30}$ alkyl group.

19. The method of claim 6, wherein any two of radicals $Q_1$, $Q_3$, $Q_4$ and $Q_5$ represent a caffeoyl group, and the other two represent an OH group, with the proviso that compounds in which either $Q_3$ or $Q_5$ represents a caffeoyl group and $Q_1$, $Q_4$ and the of other $Q_3$ or $Q_5$ represent an OH group are excluded.

20. The method of claim 6, wherein $R_{14}$ is a hydrogen atom and $R_{24}$ is a butyl group, a $C_7$-$C_{30}$ alkyl group, a $C_7$-$C_{10}$ aryyl group, or a $C_6$-$C_{18}$ aryl group covalently linked to butyl or a $C_7$-$C_{24}$ alkyl group.

21. The method of claim 11, wherein the carboxyl group activator is selected from the activators of the carbodiimide family, alone or in combination with alcohols allowing the transient formation of activated esters, or from the activators of the phosphonium, uronium and/or guanidinium salts family.

22. The method of claim 11, wherein the carboxyl group activator is selected from diisopropylcarbodiimide (DIC) and 1-hydroxybenzotriazole (HOBT).

23. The method of claim 13, wherein the inflammatory disease is selected from inflammatory diseases resulting from an excessive specific immune system response; and inflammatory diseases resulting from an excessive non-specific immune system response.

24. The method of claim 21, wherein the activators of the carbodiimide family are selected from dicyclohexylcarbodiimide (DCC), diisopropylcarbodiimide (DIC), or N-ethyl-N(3-dimethylaminopropyl)carbodiimide (EDCI); and wherein the alcohols allowing the transient formation of activated esters are selected from 1-hydroxybenzotriazole (HOBT), 1-hydroxy-7-azabenzotriazole (HOAt), 1-hydroxysuccinimide (HOSu) or ethyl (hydroxyimino)cyanoacetate; and wherein the activators of the phosphonium, uronium and/or guanidinium salts family are selected from benzotriazol-1-yloxy)tris(dimethylamino)phosphonium hexafluorophosphate (BOP), benzotriazol-1-yl-oxytripyrrolidinophosphonium hexafluorophosphate (PyBOP), (1-cyano-2-ethoxy-2-oxoethylidenaminooxy)dimethyl-amino-morpholino-carbenium hexafluorophosphate (COMU), N,N,N',N'-tetramethyl-O-(1H-benzotriazol-1-yl) uronium hexafluorophosphate (HBTU), (O-(6-chloro-1-hydrocibenzotriazol-1-yl)-1,1,3,3-tetramethyluronium tetrafluoroborate (TCTU), or (2-(7-aza-1H-benzotriazole-1-yl)-1,1,3,3-tetramethyluronium hexafluorophosphate) (HATU).

25. The method of claim 23, wherein the inflammatory diseases resulting from an excessive specific immune system response are selected from asthma, psoriasis, rhinitis, arthrosis and autoimmune diseases including Raynaud's syndrome, autoimmune thyroiditis, dermatitis, multiple sclerosis, rheumatoid arthritis, insulin-dependent diabetes mellitus, uveitis, inflammatory bowel diseases, including Crohn's disease and ulcerative colitis, and systemic lupus erythematosus; and wherein the inflammatory diseases resulting from an excessive non-specific immune system response are selected from inflammatory diseases due to adult respiratory distress syndrome, septic shock, oxygen toxicity, multiple organ dysfunction syndrome secondary to sepsis, multiple organ dysfunction syndrome secondary to trauma, tissue reperfusion injury due to extracorporeal circulation, myocardial infarction, acute glomerulonephritis, vasculitis, reactive arthritis, dermatosis with acute inflammatory components, stroke, thermal injury, haemodialysis, cytapheresis, necrotizing enterocolitis and a granulocyte transfusion associated syndrome.

\* \* \* \* \*